United States Patent
Anzaki et al.

(10) Patent No.: US 7,612,015 B2
(45) Date of Patent: *Nov. 3, 2009

(54) MEMBER HAVING PHOTOCATALYTIC FUNCTION AND METHOD FOR MANUFACTURE THEREOF

(75) Inventors: Toshiaki Anzaki, Osaka (JP); Yoshifumi Kijima, Osaka (JP); Kenji Mori, Osaka (JP)

(73) Assignee: Nippon Sheet Glass Company, Limited, Tokyo (JP)

( * ) Notice: Subject to any disclaimer, the term of this patent is extended or adjusted under 35 U.S.C. 154(b) by 565 days.

This patent is subject to a terminal disclaimer.

(21) Appl. No.: 10/499,462

(22) PCT Filed: Dec. 24, 2002

(86) PCT No.: PCT/JP02/13446

§ 371 (c)(1),
(2), (4) Date: May 20, 2005

(87) PCT Pub. No.: WO03/053577

PCT Pub. Date: Jul. 3, 2003

(65) Prior Publication Data

US 2005/0233899 A1 Oct. 20, 2005

(30) Foreign Application Priority Data

Dec. 21, 2001 (JP) ............................. 2001-389844
Jun. 14, 2002 (JP) ............................. 2002-174136

(51) Int. Cl.
| | |
|---|---|
| *B01J 21/00* | (2006.01) |
| *B01J 21/06* | (2006.01) |
| *B05D 5/00* | (2006.01) |
| *B05D 5/06* | (2006.01) |
| *B05D 1/36* | (2006.01) |
| *B05D 7/00* | (2006.01) |
| *C23C 16/00* | (2006.01) |
| *C23C 16/40* | (2006.01) |
| *C23C 28/00* | (2006.01) |
| *C23C 28/02* | (2006.01) |
| *C23C 14/00* | (2006.01) |
| *C23C 14/08* | (2006.01) |
| *C23C 14/34* | (2006.01) |

(52) U.S. Cl. ................ 502/349; 502/350; 427/162; 427/165; 427/255.11; 427/255.15; 427/255.18; 427/255.19; 427/419.1; 427/419.2; 427/419.3; 427/419.4

(58) Field of Classification Search ................ 502/242, 502/349, 350, 351, 352; 428/543; 427/162, 427/165, 255.11, 255.15, 255.18, 255.19, 427/419.1, 419.2, 419.3, 419.4

See application file for complete search history.

(56) References Cited

U.S. PATENT DOCUMENTS 3,829,197 A  8/1974 Thelen ..................... 350/164

(Continued)

FOREIGN PATENT DOCUMENTS

EP  0787696  8/1997

(Continued)

OTHER PUBLICATIONS

English-language abstract for JP 2004-513864, published May 13, 2004, PPG Industries.

(Continued)

*Primary Examiner*—Timothy C Vanoy
*Assistant Examiner*—Serena L Hanor
(74) *Attorney, Agent, or Firm*—Fredrikson & Byron, P.A.

(57) ABSTRACT

A photocatalyst layer ($TiO_2$) is formed on the surface of a substrate (glass plate) through the intermediary of a monoclinic undercoat layer ($ZrO_2$), and no dead layer is substantially present between the photocatalyst layer and the undercoat layer. Also, by providing a peel preventing layer between the substrate and the undercoat layer, it is possible to eliminate film peeling between the photocatalyst layer and the substrate, defects and discoloration. A metal element may be doped in the photocatalyst layer, and it is preferable that the metal element is at least one of Sn, Zn, Mo and Fe. The phrase "no dead layer is substantially present" means that the thickness of the dead layer is 20 nm or less. The thickness of the photocatalyst layer is preferably from 1 nm to 1,000 nm, more preferably from 1 nm to 500 nm.

26 Claims, 11 Drawing Sheets

U.S. PATENT DOCUMENTS

| | | | |
|---|---|---|---|
| 3,854,796 A | 12/1974 | Thelen | 350/164 |
| 3,934,961 A | 1/1976 | Itoh et al. | 350/164 |
| 4,322,276 A | 3/1982 | Meckel | 204/192 |
| 4,440,822 A | 4/1984 | Gordon | 428/216 |
| 4,465,575 A | 8/1984 | Love et al. | 204/192 |
| 4,814,056 A | 3/1989 | Welty | 204/298 |
| 5,194,990 A | 3/1993 | Boulos | 359/587 |
| 5,254,392 A | 10/1993 | Burns et al. | 428/212 |
| 5,342,676 A | 8/1994 | Zagdoun | 428/216 |
| 5,780,149 A | 7/1998 | McCurdy et al. | 428/336 |
| 5,811,191 A | 9/1998 | Neuman | 428/427 |
| 5,891,556 A | 4/1999 | Anderson et al. | 428/216 |
| 5,935,716 A | 8/1999 | McCurdy et al. | 428/428 |
| 5,965,246 A | 10/1999 | Guiselin et al. | 428/212 |
| 6,027,766 A | 2/2000 | Greenberg et al. | 427/226 |
| 6,027,797 A | 2/2000 | Watanabe | |
| 6,037,289 A | 3/2000 | Chopin et al. | 502/2 |
| 6,068,914 A | 5/2000 | Boire et al. | 428/216 |
| 6,103,363 A | 8/2000 | Boire et al. | 428/325 |
| 6,114,043 A | 9/2000 | Joret | 428/428 |
| 6,165,598 A | 12/2000 | Nelson | 428/212 |
| 6,193,378 B1 | 2/2001 | Tonar et al. | 359/603 |
| 6,352,755 B1 | 3/2002 | Finley et al. | 428/100 |
| 6,354,109 B1 | 3/2002 | Boire et al. | 65/60.1 |
| 6,677,063 B2 * | 1/2004 | Finley | 428/701 |
| 6,761,984 B2 * | 7/2004 | Anzaki et al. | 428/697 |
| 6,833,089 B1 * | 12/2004 | Kawahara et al. | 252/520.2 |
| 2002/0004289 A1 | 1/2002 | Gosain | |
| 2002/0004291 A1 | 1/2002 | Yamazaki | |
| 2002/0045073 A1 | 4/2002 | Finley | 428/701 |
| 2003/0024180 A1 | 2/2003 | Hartig | |
| 2004/0146721 A1 | 7/2004 | Hartig | |
| 2007/0031681 A1 | 2/2007 | Anzaki | |
| 2007/0082205 A1 | 4/2007 | Anzaki | |
| 2007/0237968 A1 | 10/2007 | Kijima | |

FOREIGN PATENT DOCUMENTS

| | | |
|---|---|---|
| EP | 1132351 A1 | 9/2001 |
| EP | 1253214 A1 | 10/2002 |
| EP | 1300374 A | 4/2003 |
| FR | 2738813 A | 3/1997 |
| JP | 7-315889 | 12/1995 |
| JP | 8-104547 | 4/1996 |
| JP | 9-227167 | 9/1997 |
| JP | 9-313948 A | 12/1997 |
| JP | 10-66878 | 3/1998 |
| JP | 10-278165 | 10/1998 |
| JP | 11-511109 | 9/1999 |
| JP | 11-512337 A | 10/1999 |
| JP | 2000-312830 | 11/2000 |
| JP | 2000-313695 A | 11/2000 |
| JP | 2001-009295 A | 1/2001 |
| JP | 2001046881 A | 2/2001 |
| JP | 2001-121003 A | 5/2001 |
| JP | 2001-205094 | 7/2001 |
| JP | 2001-212581 A | 8/2001 |
| JP | 2001240960 A | 9/2001 |
| JP | 2002-030417 | 1/2002 |
| JP | 2002-524383 | 8/2002 |
| JP | 2003-112054 | 4/2003 |
| WO | WO 97/10186 A1 | 3/1997 |
| WO | WO 98/41480 A1 | 9/1998 |
| WO | 0146488 A1 | 6/2001 |
| WO | 0218287 A1 | 3/2002 |
| WO | WO 02/40417 A2 | 5/2002 |
| WO | 02/062716 | 8/2002 |
| WO | WO 03/053577 A1 | 7/2003 |
| WO | 02/40417 | 5/2009 |

OTHER PUBLICATIONS

Partial English-language translation of JP 2001-121003, published May 8, 2001, Nippon Sheet Glass.

Supplemental European Search Report, dated Nov. 13, 2007 for European Application No. 02790849.0, 5 pages.

Japanese Office Action, dated Jun. 26, 2008 for Japanese Application No. 2003-554330, 5 pages.

English-language abstract for JP 2000-513695, published Oct. 17, 2000, PPG Industries.

English-language abstract for JP 2001046881, published Feb. 20, 2001, Nippon Sheet Glass.

English-language abstract for JP 2001-240960, published Sep. 4, 2001, Nippon Sheet Glass.

English translation of JP 8-104547, published Apr. 23, 1996, Nippon Sheet Glass.

G.R. Lumpkin, "Physical and chemical characteristics of baddeleyite (monoclinic zirconia) in natural environments: an overview and case study", Journal of Nuclear Materials, vol. 274, No. 1, Aug. 2, 1999, 2 pages.

The Mineral Anatase (website) http://web.archive.org/web/20000303215934/http://mineral.galleries.com/minerals/ oxides/..., printed Jul. 15, 2008, 2 pages.

Non Final Office Action, dated Jul. 24, 2008 for U.S. Appl. No. 11/758,360, 11 pages.

Response to Non Final Office Action, dated Dec. 8, 2008 for U.S. Appl. No. 11/758,360, 10 pages.

Final Office Action, dated Mar. 30, 2009 for U.S. Appl. No. 11/758,360, 15 pages.

English-language abstract for JP 7-315889, published Dec. 5, 1995, Nippon Sheet Glass.

English-language abstract for JP 10-66878, published Mar. 10, 1998, Bridgestone Corp.

English-language abstract for JP 10-278165, published Oct. 20, 1998, Asahi Glass Co.

English-language abstract for JP 11-511109, published Sep. 28, 1999, Heller.

English-language abstract for JP 2002-030417, published Jan. 31, 2002, Japan Atomic Energy.

English-language abstract for JP 2002-524383, published Aug. 6, 2002, PPG Industries.

English-language abstract for JP 2003-112054, published Apr. 15, 2003, Mitsubishi Heavy Ind.

Non Final Office Action, dated Jul. 22, 2008 for U.S. Appl. No. 10/560,053, 11 pages.

Non Final Office Action, dated Jul. 25, 2008 for U.S. Appl. No. 10/560,694, 15 pages.

\* cited by examiner (a) ZrO₂(111)

(b) TiO₂(101)

(a)

(b)

(c)

(d)

MEMBER HAVING PHOTOCATALYTIC FUNCTION AND METHOD FOR MANUFACTURE THEREOF

TECHNICAL FIELD

The present invention relates to a member with a photocatalyst layer formed on the surface thereof.

BACKGROUND ART

Photocatalysts such as anatase type titanium oxide are known to exert antifouling effect to decompose organic materials under ultraviolet light irradiation, antibacterial activity and hydrophilicity. Additionally, nowadays, photocatalysts exerting a catalytic function under visible light irradiation are attracting attention.

Formation of the above-described photocatalyst layer on the surface of a member such as glass is frequently carried out by means of vacuum film formation methods including sputtering and vapor deposition, or reduced-pressure film-formation methods.

Provision of an undercoat layer between the substrate such as glass and the photocatalyst layer formed on the surface of the substrate has been proposed in Japanese Patent Application Publication No. 9-227167, Japanese Patent Application Publication No. 10-66878, Japanese Patent Application Publication No. 2000-312830, and Japanese Patent Application Publication No. 2001-205094.

Japanese Patent Application Publication No. 9-227167 discloses that a barrier layer is provided between a glass substrate and a photocatalytic composition (medium) which is formed on the surface of the substrate for the purpose of preventing function deterioration of the medium caused by alkali eluted from the glass, and proposes use of zirconium oxide, in particular, amorphous zirconium oxide as the barrier layer.

Japanese Patent Application Publication No. 10-66878 discloses that a photocatalyst film is formed on a substrate in a state where an undercoat film is interposed therebetween, and in particular, zirconium oxide is used as the undercoat film and titanium oxide is used as the photocatalyst film.

Japanese Patent Application Publication No. 2000-312830 discloses that a layer of a metal oxide such as zirconium oxide is interposed between a substrate (aluminum) and a photocatalyst layer so as to control oxygen diffusion from the photocatalyst layer to the substrate with the aid of the metal oxide layer.

Japanese Patent Application Publication No. 2001-205094 discloses zirconium oxide as a photocatalytic material and discloses that a titanium oxide layer is formed on the exterior of the zirconium oxide.

PCT International Publication (WO 02/40417) discloses that a high temperature stable type cubic or orthorhombic zirconium oxide layer is formed between a substrate and a titanium oxide layer.

When a photocatalyst layer is formed according to the above-described methods, there are cases where no photocatalytic function is exerted, or such a function is not exerted unless the thickness of the photocatalyst layer is made thick, which causes the reflectance of the article to become large and interference color to be generated, and thereby the compatibility of the preferable reflectance and color tone with the photocatalytic activity is hardly achieved. Also, there are drawbacks that when a high temperature stable type cubic or orthorhombic zirconium oxide layer needs to be formed, low heat resistance resin and the like cannot be used as a substrate, and photocatalytic members having a large size for use in construction and the like can be hardly obtained because it is technically difficult to heat large size substrates uniformly.

DISCLOSURE OF THE INVENTION

In order to solve the above-described problems, researches were made by the present inventors, and it turned out that difference in the degree of crystal growth in a photocatalyst layer causes a state where some of photocatalyst layers ($TiO_2$) exert and others do not exert a photocatalytic function depending on the film configuration and the film-formation conditions even if the photocatalyst layers have the same film thickness. More specifically, a photocatalyst layer ($TiO_2$) in which a columnar particulate structure of polycrystal or single crystal is formed clearly and continuously from the interface of the substrate to the surface of the photocatalyst layer exerts a remarkable photocatalytic effect; however, a photocatalyst layer ($TiO_2$), in which no columnar particulate structure is found in the neighborhood of the interface of the substrate and an amorphous layer (hereinafter referred to as a dead layer) is found instead does not exert any sufficient photocatalytic effect. Accordingly, the present inventors investigated measures for substantially preventing the above-described dead layer from being formed, and discovered that provision of an undercoat layer for promoting crystal growth in the photocatalyst layer can effectively control formation of the dead layer.

However, in the case of a configuration in which the above-described dead layer is substantially absent, since a particulate structure is formed from the undercoat layer to the photocatalyst layer, there are cases where chlorine ions and water pass through the voids in the particulate structure (columnar structure) and diffuse from the surface toward the glass substrate. When such diffusing molecules reach the glass substrate, there are cases where anions such as chlorine ions react with alkali ions such as sodium contained in the glass substrate so as to generate salt, which causes film peeling or defects. In order to prevent such phenomena, provision of a peel preventing layer between the undercoat layer and the substrate has been found to be effective.

The present inventors have achieved the present invention on the basis of the following knowledge:

When a photocatalyst layer is formed through the intermediary of an undercoat layer which promotes the crystal growth of the photocatalyst, the generation of the above-described dead layer can be controlled, and when a peel preventing layer is provided between the undercoat layer and the glass substrate, peeling of the film from the glass substrate and the generation of defects can be controlled. In addition, an excellent photocatalytic function can be achieved even if the film formation is conducted at low temperature.

Specifically, according to the present invention, there is provided a member having a photocatalytic function in which a photocatalyst layer is formed on the surface of a substrate through the intermediary of a crystalline undercoat layer, and no dead layer is substantially present in the neighborhood of the interface between the photocatalyst layer and the undercoat layer.

According to the present invention, there is also provided a member having a photocatalytic function in which a peel preventing layer whose main component is an oxide, and oxynitride and a nitride containing at least one of silicon and tin is provided on the surface of a substrate, a photocatalyst layer is formed on the surface of the peel preventing layer through the intermediary of a crystalline undercoat layer, and no dead layer is substantially present between the undercoat layer and the photocatalyst layer. The thickness of the peel preventing layer is 2 nm to 200 nm, preferably 5 nm to 50 nm. When the thickness of the peel preventing layer is less than 2 nm, the effect of controlling the generation of peeling and defects becomes insufficient. On the other hand, even when the thickness of the peel preventing layer is greater than 200 nm, the effect of controlling the generation of peeling and defects is not largely improved. Therefore, the upper limit of the thickness of the peel preventing layer is preferably 200 nm from the viewpoint of economy. When the thickness of the peel preventing layer is greater than 5 nm, the water blocking effect more preferably is enhanced. In addition, when the thickness exceeds 50 nm, the stress of the amorphous film becomes greater and peeling easily occurs. Therefore, the more preferable upper limit of the thickness of the peel preventing layer is 50 nm.

An embodiment of the member having a photocatalytic function according to the present invention has a configuration in which a photocatalyst layer is formed on the surface of a substrate through the intermediary of a crystalline undercoat layer, the substrate is a glass substrate manufactured by a float glass method, the undercoat layer is positioned on the tin-containing surface (namely, the tin modification layer or the amorphous tin oxide layer) of the glass substrate, and no dead layer is substantially present between the undercoat layer and the photocatalyst layer.

Provision of the crystalline undercoat layer can improve the crystallinity of the photocatalyst layer, and the surface of the photocatalyst layer can be rapidly made superhydrophilic. Also, provision of the peel preventing layer between the substrate and the crystalline undercoat layer can control peeling of the undercoat layer from the substrate, or defects.

The peel preventing layer whose main component is an oxide, an oxynitride and a nitride containing at least one of silicon and tin has a capability of blocking a variety of ions and molecules such as a chlorine ion and water which penetrate from the outside. Also, when a glass plate manufactured by a float process (for example, a method for manufacturing a glass plate by floating molten glass on molten tin) is used as the substrate, a tin oxide containing layer (tin modification layer) is located on the bottom face (which refers to the face in contact with tin; the top face refers to the face not in contact with tin), and this layer functions as the peel preventing layer.

The peel preventing layer blocks chlorine ions and water which penetrate from the surface, prevents these ions and molecules from reaching the glass substrate, and thereby, it is possible to control peeling of the undercoat layer from the substrate. It is also possible to control discoloration or defects caused by reaction of carbonic acid gas and water from the atmosphere with alkali components in the glass.

The dead layer is a layer in which amorphous (noncrystalline) characteristics are predominant, and the electron diffraction image is observed as a halo pattern as shown in FIG. 1(a). On the other hand, in a case where a layer is different from a dead layer, diffraction spots are observed as shown in FIG. 1(b).

The phrase that "no dead layer is substantially present" refers to a case where the thickness of the dead layer is 20 nm or less, or more preferably 10 nm or less, as well as a case where no dead layer is present. The dead layer having such a thickness does not cause so much deterioration of the photocatalytic activity which is caused by deterioration of the crystallinity of the photocatalyst layer.

The thickness of the photocatalyst layer is preferably 1 nm to 1,000 nm. When the thickness is less than 1 nm, the continuity of the film becomes poor and photocatalytic activity becomes insufficient. In contrast, when the thickness is greater than 1,000 nm, since exciting light (ultraviolet light) does not reach the deep interior of the photocatalyst layer, such an increase of the film thickness does not lead to any further improvement of the photocatalytic activity. In particular, the effect of the undercoat layer is found to be remarkable in a case where the thickness is in the range from 1 nm to 500 nm. A comparison made with respect to the same thickness showed that the case where the undercoat layer is provided presents a larger photocatalytic activity than the case where no undercoat layer is provided. Therefore, it can be said that the thickness range of from 1 nm to 500 nm is more preferable.

Even when the thickness of the photocatalyst layer is made as thin as 1 nm to 100 nm, if the particulates constituting the photocatalyst layer are formed continuously from the interface of the undercoat layer to the surface of the photocatalyst layer, crystal growth is developed, and thereby the photocatalytic activity can be exerted sufficiently.

The width of the particulates constituting the photocatalyst layer along the direction parallel to the substrate is preferably 5 nm or more. This is because if particulate width is less than 5 nm, the crystallinity is low and the photocatalytic activity becomes insufficient.

Also, in the present invention, it is preferable that the undercoat layer and the photocatalyst layer are made of a crystalline metal oxide or a crystalline metal oxynitride, and at least one of the distances between oxygen atoms in the crystals which constitute the undercoat layer is approximate to one of the distances between oxygen atoms in the crystals which constitute the photocatalyst layer. When the photocatalyst layer is formed on the undercoat layer, a combination of the undercoat layer and the photocatalyst layer which satisfies the above-described condition allows the photocatalyst layer to grow easily and quickly as a crystalline one with the aid of the oxygen atoms as the common portions.

FIG. 2(a) shows the atomic arrangement in the (111) orientation plane in the monoclinic zirconium oxide, and FIG. 2(b) shows the atomic arrangement in the (101) orientation plane in the tetragonal (anatase type) titanium oxide. With respect to the distances between oxygen atoms, the monoclinic zirconium oxide and the tetragonal (anatase type) titanium oxide are similar to each other (in the range of from 90 to 110%). Accordingly, if the monoclinic crystalline zirconium compound is used as the undercoat layer, the crystalline film of the tetragonal titanium oxide can be formed on the undercoat layer easily.

As for the undercoat layer, zirconium oxide to which a small amount of nitrogen is added, zirconium oxynitride, and zirconium oxide to which niobium (Nb) of 0.1 to 10 atomic % is added are preferably used as well as the above-described monoclinic zirconium oxide. When a target to which niobium is added is used for sputtering, generation of arcing can be prevented, and undesirable power control and deterioration of the film formation rate can be prevented.

As for the photocatalyst layer, the above-described tetragonal titanium oxide is preferably used. In particular, anatase type titanium oxide is preferably used because the photocatalytic activity thereof is high. In addition to anatase type titanium oxide, rutile type titanium oxide, a composite oxide of titanium and tin, a mixed oxide of titanium and tin, titanium oxide to which a small amount of nitrogen is added, and titanium oxynitride are preferably used.

The thickness of the undercoat layer is preferably 1 nm or more and 500 nm or less. The thickness of less than 1 nm is not preferable because the undercoat layer of such a thickness is not continuous and island-like, and thereby the durability is decreased. On the other hand, even when the thickness is greater than 500 nm, the effect of the thickness on the photocatalyst layer becomes substantially the same, and increasing the thickness is economically useless. The more preferable thickness of the undercoat layer is 2 to 50 m-n. When the thickness is less than 2 nm, the crystallinity of the undercoat layer becomes low, and hence the effect of promoting the crystal growth of the photocatalyst layer becomes small. When the thickness is greater than 50 nm, the variation of the optical properties (color tone, reflectance) due to the thickness variation becomes large.

As for the monoclinic zirconium oxide which is preferable for the undercoat layer, the electron diffraction image obtained by perpendicularly irradiating the cross section of the layer of the monoclinic zirconium oxide includes the electron diffraction image from the (111) plane or the (−111) plane, and the interplanar spacing with respect to the (111) orientation plane measured by the above-described electron diffraction image or by a bright-field image of a transmission electron microscope (TEM) is 2.6 to 3.0 Å, and the interplanar spacing with respect to the (−111) orientation plane measured by the same method is 3.0 to 3.5 Å.

In a case where the interplanar spacing of zirconium oxide is not in the above-described ranges, the zirconium oxide suffers from deformation in the crystals. Consequently, the film stress becomes great, and peeling easily occurs. Also, since the oxygen positions in the crystal planes are displaced due to the deformation, the consistency of the oxide such as titanium oxide or the like constituting the photocatalyst layer with the oxygen positions becomes low, and thereby no desirable crystal growth of the photocatalyst layer is observed.

As for the anatase type titanium oxide which is preferable for the photocatalyst layer, the electron diffraction image obtained by perpendicularly irradiating the cross section of the layer of the anatase type titanium oxide includes the electron diffraction pattern from the (101) plane, and the interplanar spacing with respect to the (101) orientation plane measured by the above-described electron diffraction image or by a bright-field image of a transmission electron microscope (TEM) is 3.3 to 3.7 Å.

In a case where the interplanar spacing of titanium oxide is not in the above-described spacing range, the titanium oxide suffers from deformation in the crystals. Consequently, the film stress becomes great, and peeling easily occurs. Also, since the oxygen positions in the crystal planes are displaced due to the deformation, the consistency of the oxide such as zirconium oxide or the like constituting the undercoat layer with the oxygen positions becomes low, and thereby no desirable crystal growth of the titanium oxide is observed.

The methods for forming the undercoat layer and the photocatalyst layer may be any of a liquid phase method (a sol-gel method, a liquid phase precipitation method, a spray method and a pyrosol method), a vapor phase method (a sputtering method, a vacuum deposition method and a CVD method) and the like, and these methods have the effect of improving the crystallinity of the photocatalyst layer with the aid of the undercoat layer. However, a vapor phase method such as a sputtering method, a deposition method and the like is more suitable because it is serves to grow crystals, and thereby it shows particularly significant effect in the present invention.

Additionally, doping of metals in the photocatalyst layer can promote carrier generation and accordingly enhance the photocatalytic effect.

Examples of the doped metals include Sn, Zn, Mo and Fe, which are suitably high in the effect of improving the photocatalytic activity. With respect to Sn, Zn and Mo, the addition amount is preferably 0.1 mass % or more and 1 mass % or less, more preferably 0.2 mass % or more and 0.5 mass % or less. With respect to Fe, the content thereof in the photocatalyst layer is made to be 0.001 mass % to 1.0 mass %. These limitations are based on the fact that the effect becomes too small in a case where the addition amount is too small, while too great an amount causes disorder in the crystal structure of the photocatalyst and generation of a recombination center, and thereby the photocatalytic activity is deteriorated.

Titanium tin composite oxide or titanium tin mixed oxide is used for the photocatalyst layer. By using titanium oxide containing tin, it is possible to improve the maintenance of the hydrophilicity without deteriorating the photocatalytic activity of titanium oxide ($TiO_2$). In a case of forming a film by a sputtering method, the effect of tin contained in the target improves the film formation rate. The content of tin in the photocatalyst layer is 3 atomic % or more and 50 atomic % or less based on the ratio of the number of tin atoms with respect to the total number of titanium atoms and tin atoms. When the content of tin is less than 3 atomic %, the effect of the addition of tin is unpreferably small. On the other hand, when the content of tin is greater than 50 atomic %, the photocatalytic activity is unpreferably deteriorated.

By forming a hydrophilic thin film on the surface of the photocatalyst layer, it is possible to increase the hydrophilic effect. The hydrophilic thin film is preferably made of at lease one oxide selected from the group consisting of silicon oxide, zirconium oxide, germanium oxide and aluminum oxide. Among these oxides, silicon oxide is preferable from the viewpoint of the hydrophilicity improvement effect and durability. It is preferable that the hydrophilic thin film is porous. When the hydrophilic thin film is porous, it is possible to enhance the water holding effect and the maintenance performance of the hydrophilicity. Also, the active species such as active oxygen generated in the surface of the photocatalyst layer by irradiation of ultraviolet light can reach the surface of an article, so that the photocatalytic activity of the photocatalyst layer is not so significantly damaged.

As the method for forming a porous hydrophilic thin film, a liquid phase method (a sol-gel method, a liquid phase precipitation method, and a spray method) and a vapor phase method (a sputtering method, a vacuum deposition method and a CVD method) are used. If the generally known sol-gel method is employed, a porous thin film can be manufactured easily; however, when organic polymer and higher alcohol are added into the raw material solution of the sol gel method, a porous thin film can be manufactured more easily. As for the vapor phase method such as a sputtering method, by adjusting the film formation conditions so as to increase the dangling bonds in the oxide, for example, by increasing the gas pressure and reducing the oxygen amount in the gas at the time of sputtering, it becomes possible to manufacture a porous thin film.

The thickness of the hydrophilic thin film is preferably 1 nm or more and 30 nm or less. If the thickness is smaller than 1 nm, the hydrophilicity is insufficient, while if the thickness is greater than 30 nm, the photocatalytic activity of the photocatalyst layer is damaged. The more preferable range of the thickness is 1 nm or more and 20 nm or less. In this range, the maintenance performance of the hydrophilicity is high when it is not irradiated with light.

The method of manufacturing the photocatalytic member according to the present invention comprises the steps of forming a peel preventing layer whose main component is an oxide, an oxynitride and a nitride containing at least one of silicon and tin on the surface of a substrate, forming a monoclinic zirconium oxide layer at low temperature on the peel preventing layer, and forming a photocatalyst layer constituted of a crystalline phase on the monoclinic zirconium oxide layer. With this, a photocatalytic member is obtained in which a dead layer observed as a halo pattern in an electron diffraction image is not substantially present between the monoclinic zirconium oxide layer and the photocatalyst layer. As the method for forming the monoclinic zirconium oxide layer, a vapor phase method, in particular, a sputtering method is preferable.

As described above, according to the present invention, a photocatalyst layer having high photocatalytic activity can be formed, without heating or at temperature of 150° C. or below, on a substrate or a thin film having low heat resistance, and thereby it becomes possible to combine a photocatalyst layer with a component having low heat resistance. Also, the present invention can be applied to film formation on a large size substrate such as glass in which uniform heating and control of cracks which may occur at the time of heating and cooling are difficult. Examples of the above-described substrate having low heat resistance include a resin substrate or a film made of acrylic resin, polyethylene terephthalate resin, polyurethane resin, polyimide resin and the like.

BEST MODE FOR CARRYING OUT THE INVENTION

Figure 1:
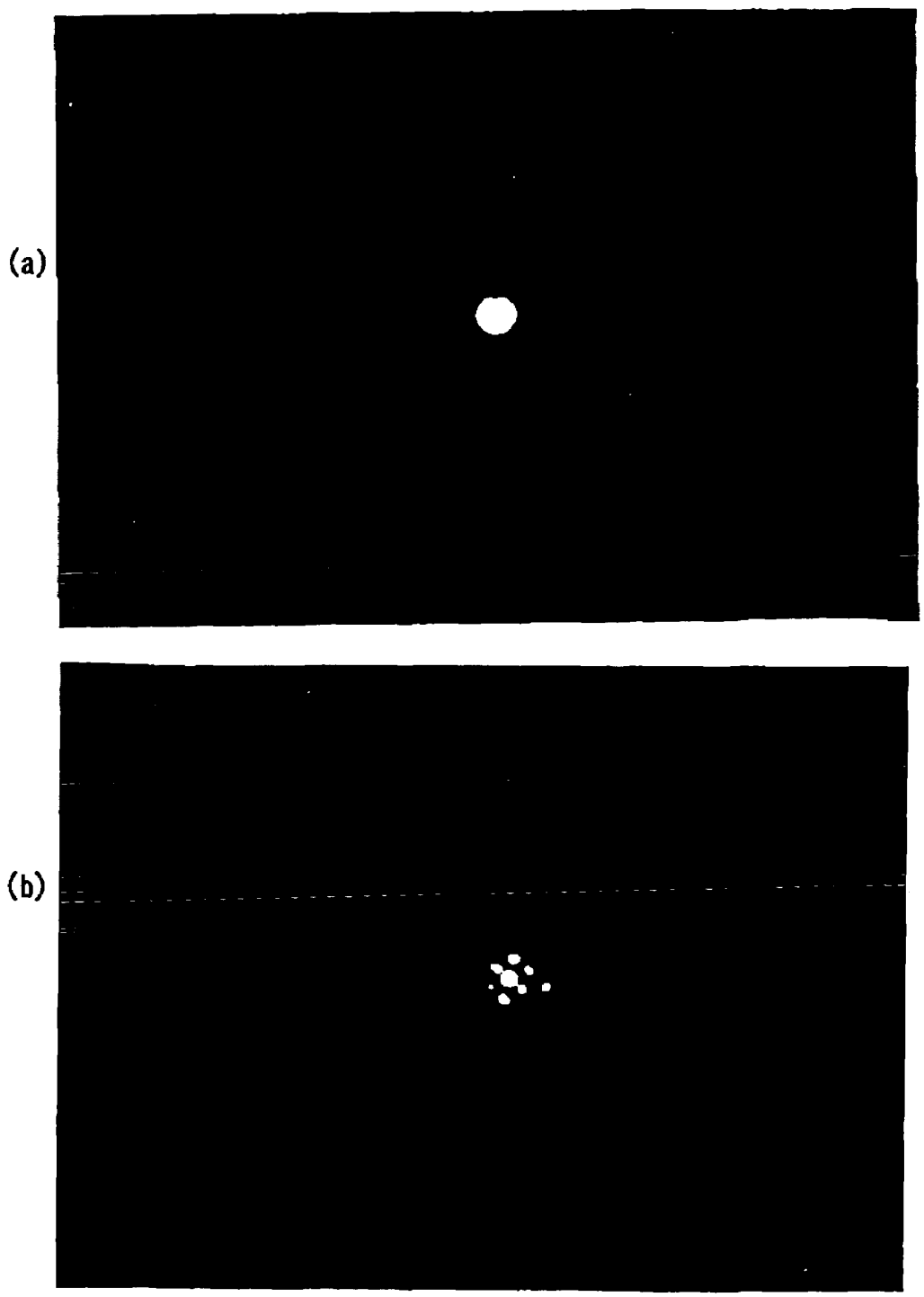
FIG. 1(a) is a transmission electron microscope (TEM) observation picture showing the electron diffraction pattern in a case where a dead layer is present.
FIG. 1(b) is a TEM picture showing the electron diffraction pattern in a case where no dead layer is present.
Figure 2:
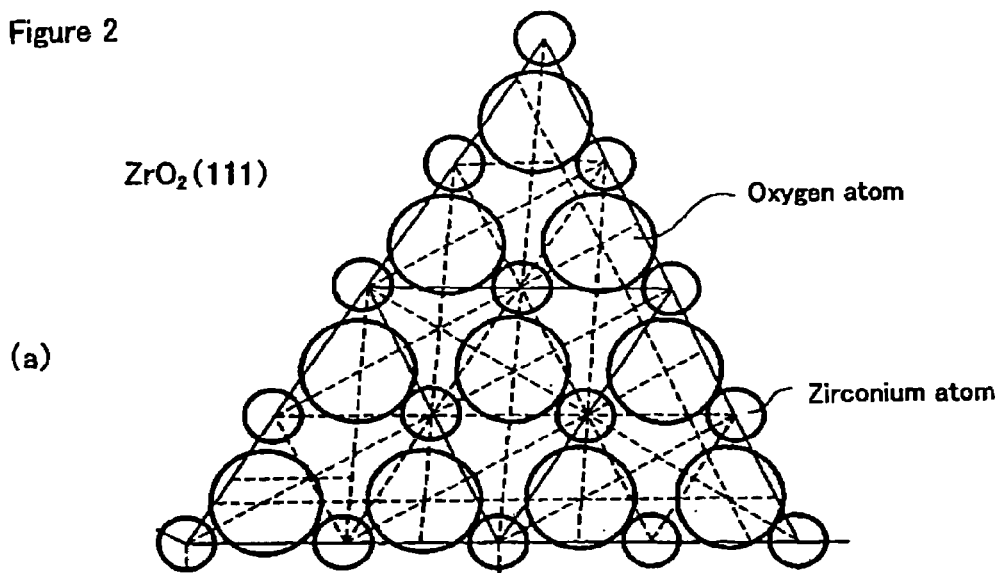
FIG. 2(a) is a diagram illustrating the atomic arrangement in the (111) plane of monoclinic zirconium oxide.
FIG. 2(b) is a diagram illustrating the atomic arrangement in the (101) plane of anatase type titanium oxide.
Figure 2:
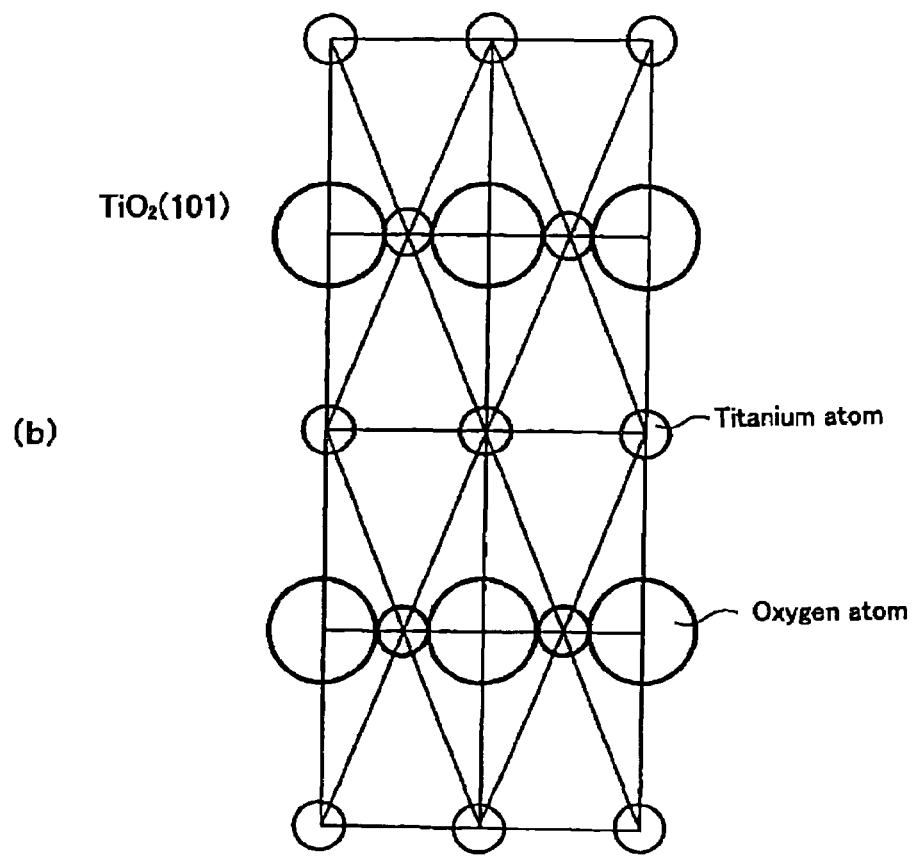
Figure 3:
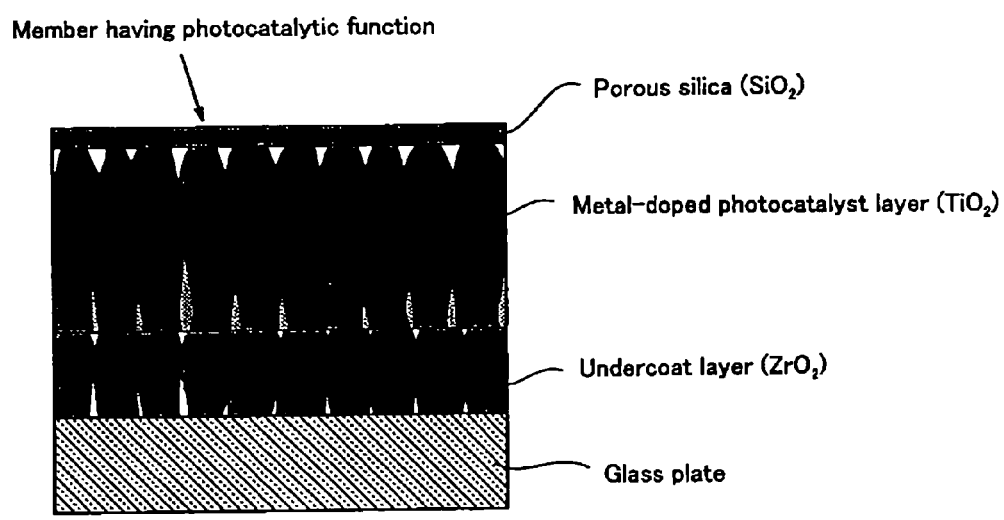
FIG. 3 is a schematic cross-sectional view illustrating a member having a photocatalytic function according to the present invention.

A detailed description will be made below on embodiments of the present invention referring to the accompanying drawings. FIG. 3 is a schematic cross-sectional view illustrating a member having a photocatalytic function according to the present invention. In this typical example, a layer of crystalline $ZrO_2$ is formed as an undercoat layer in a thickness of 56 nm on the surface of a glass plate as a substrate, a layer of crystalline $TiO_2$ in which metal is doped is formed as a photocatalyst layer in a thickness of 140 nm on the $ZrO_2$ layer, and a porous $SiO_2$ layer is formed in a thickness of 5 nm on the $TiO_2$ layer so as to enhance the hydrophilicity.

The above-described $ZrO_2$ layer, $TiO_2$ layer and $SiO_2$ layer are formed by a sputtering method. Metal such as tin (Sn), zinc (Zn), molybdenum (Mo) or iron (Fe) is doped at the time of forming the $TiO_2$ layer.

Table 1 shows the film configuration, the methods for forming the peel preventing layer, the undercoat layer, the photocatalyst layer and the hydrophilic thin layer, the presence of a dead layer, and the evaluation of the contact angle in Examples 1 to 9. Table 2 shows the film configuration, the methods for forming the peel preventing layer, the undercoat layer, the photocatalyst layer and the hydrophilic thin layer, the presence of a dead layer, and the evaluation of the contact angle in Comparative Examples 1 to 11. Table 3 shows the film formation conditions for each film in Table 1 and Table 2 (i.e., the peel preventing layer, the undercoat layer, the photocatalyst layer and the hydrophilic film).

TABLE 1

| | | Film configuration and film formation method | | | | Electron | Contact angle evaluation results | |
| --- | --- | --- | --- | --- | --- | --- | --- | --- |
| | Substrate | Peel preventing layer (thickness) Film formation method | Undercoat layer (thickness) Film formation method | Photocatalyst layer (thickness) Film formation method | Hydrophilic thin layer (thickness) Film formation method | diffraction & TEM measurement Presence/ absence of dead layer | UV-01 method Contact angle after UV irradiation Overall evaluation | UV-02 method (UV irradiation, stored in dark) Overall evaluation |
| Ex. 1 | Glass | $SiO_2$ (20 nm) Sputtering | Monoclinic $ZrO_2$ (56 nm) Sputtering | Anatase $TiO_2$ (140 nm) Sputtering | | Absent | 5° E | |
| Ex. 2 | Glass | $SiO_2$ (20 nm) Sputtering | Monoclinic $ZrO_2$ (56 nm) Sputtering | Anatase $TiO_2$ (140 nm) Sputtering | | Absent | 4° E | |
| Ex. 3 | Glass | | Monoclinic $ZrO_2$ (56 nm) Deposition | Anatase $TiO_2$ (140 nm) Deposition | | Present (15 nm) | 10° G | |
| Ex. 4 | Glass | | Monoclinic $ZrO_xN_y$ (56 nm) Sputtering | Anatase $TiO_xN_y$ (140 nm) Sputtering | | Present (5 nm) | 6° G | |

TABLE 1-continued

| | Substrate | Peel preventing layer (thickness) Film formation method | Undercoat layer (thickness) Film formation method | Photocatalyst layer (thickness) Film formation method | Hydrophilic thin layer (thickness) Film formation method | Electron diffraction & TEM measurement Presence/absence of dead layer | Contact angle evaluation results UV-θ1 method Contact angle after UV irradiation Overall evaluation | UV-θ2 method (UV irradiation, stored in dark) Overall evaluation |
|---|---|---|---|---|---|---|---|---|
| Ex. 5 | Glass | | Monoclinic $ZrO_2$ (56 nm) Deposition | Anatase $TiO_2$ (140 nm) Deposition | | Present (10 nm) | 7° G | |
| Ex. 6 | Glass | | Monoclinic $ZrO_2$ (56 nm) Sputtering | Zn (0.42 wt %) doped $TiO_2$ (140 nm) Sputtering | | Absent | 1° E | |
| Ex. 7 | Glass | | Monoclinic $ZrO_2$ (56 nm) Sputtering | Mo (0.35 wt %) doped $TiO_2$ (140 nm) Sputtering | | Absent | 2° E | |
| Ex. 8 | Glass | | Monoclinic $ZrO_2$ (56 nm) Sputtering | Fe (0.05 wt %) doped $TiO_2$ (140 nm) Sputtering | | Absent | 2° E | |
| Ex. 9 | Glass | | Monoclinic $ZrO_2$ (56 nm) Sputtering | Zn (0.42 wt %) doped $TiO_2$ (140 nm) Sputtering | $SiO_2$ (5 nm) Sputtering | Absent | | (4°, 10°) E |

TABLE 2

| | Substrate | Peel preventing layer (thickness) Film formation method | Undercoat layer (thickness) Film formation method | Photocatalyst layer (thickness) Film formation method | Hydrophilic thin layer (thickness) Film formation method | Electron diffraction & TEM measurement Presence/absence of dead layer | Contact angle evaluation results UV-θ1 method (Contact angle after UV irradiation) Overall evaluation | UV-θ2 method (UV irradiation, stored in dark) Overall evaluation |
|---|---|---|---|---|---|---|---|---|
| Com. ex. 1 | Glass | $SiO_2$ (20 nm) Sputtering | Amorphous $Si_3N_4$ (60 nm) Sputtering | Low crystallinity $TiO_2$ (140 nm) Sputtering | | Present (45 nm thick) | 32° B | (33°, 53°) B |
| Com. ex. 2 | Glass | $SiO_2$ (20 nm) Sputtering | | Low crystallinity $TiO_2$ (140 nm) Sputtering | | Present (50 nm thick) | 35° B | |
| Com. ex. 3 | Glass | | Amorphous $ZrO_2$ (56 nm) Transition mode sputtering | Low crystallinity $TiO_2$ (140 nm) Sputtering | | Present (40 nm thick) | 29° B | |
| Com. ex. 4 | Glass | | Amorphous $ZrO_2$ (56 nm) Ion assisted deposition | Low crystallinity $TiO_2$ (140 nm) Deposition | | Present (50 nm thick) | 38° B | |
| Com. ex. 5 | Glass | | | Zn (0.42 wt %) doped $TiO_2$ (140 nm) Low crystallinity↑ Sputtering | | Present (50 nm thick) | 20° B | |
| Com. ex. 6 | Glass | | | Zn (1.5 wt %) doped $TiO_2$ (140 nm) Low crystallinity↑ Sputtering | | Present (50 nm thick) | 40° B | |
| Com. ex. 7 | Glass | | | Mo (0.35 wt %) doped $TiO_2$ (140 nm) Low crystallinity↑ Sputtering | | Present (50 nm thick) | 22° B | |
| Com. ex. 8 | Glass | | | Mo (1.5 wt %) doped $TiO_2$ (140 nm) Low crystallinity↑ Sputtering | | Present (50 nm thick) | 40° B | |

TABLE 2-continued

| | | Film configuration and film formation method | | | | Electron diffraction & TEM measurement Presence/absence of dead layer | Contact angle evaluation results | |
|---|---|---|---|---|---|---|---|---|
| | Substrate | Peel preventing layer (thickness) Film formation method | Undercoat layer (thickness) Film formation method | Photocatalyst layer (thickness) Film formation method | Hydrophilic thin layer (thickness) Film formation method | | UV-θ1 method (Contact angle after UV irradiation) Overall evaluation | UV-θ2 method (UV irradiation, stored in dark) Overall evaluation |
| Com. ex. 9 | Glass | | | Fe (0.05 wt %) doped TiO$_2$ (140 nm) Low crystallinity↑ Sputtering | | Present (50 nm thick) | 24° B | |
| Com. ex. 10 | Glass | | | Mo (0.1 wt %) doped TiO$_2$ (140 nm) Low crystallinity↑ Sputtering | | Present (50 nm thick) | 37° B | |
| Com. ex. 11 | Glass | | | Low crystallinity TiO$_2$ (140 nm) Low crystallinity↑ Sputtering | SiO$_2$ (5 nm) Sputtering | Present (50 nm thick) | (35°, 38°) B | |

TABLE 3

Film formation conditions (Film formation conditions in Tables 1 and 2)

1) Undercoat layer

| | ZrO$_2$ | | | | | ZrOxNy | ZrO$_2$ | Si$_3$N$_4$ (SiN) |
|---|---|---|---|---|---|---|---|---|
| | Sputtering | Sputtering | Transition mode sputtering | Deposition | Ion assisted deposition | Sputtering | Deposition | Sputtering |
| Target | Zr | Zr | Zr | ZrO | ZrO | Zr | ZrO | Si |
| Gas | O$_2$: 100% | O$_2$: 100% | O$_2$: 30%, Ar 70% | O$_2$: 100% | O$_2$: 100% | O$_2$: 97%, N$_2$: 3% | O$_2$: 50%, Ar: 50% | N$_2$: 100% |
| Gas pressure | 0.93 Pa (7 m Torr) | 2.0 Pa (15 m Torr) | 0.93 Pa (7 m Torr) | 1.33 × 10$^{-2}$ Pa (1 × 10$^{-4}$ Torr) | 1.33 × 10$^{-2}$ Pa (1 × 10$^{-4}$ Torr) | 0.93 Pa (7 m Torr) | 1.33 × 10$^{-2}$ Pa (1 × 10$^{-4}$ Torr) | 0.93 Pa (7 m Torr) |
| Applied power, etc. | RF 2.0 kW | RF 2.0 kW | DC pulse 100 khz 2.0 kW | 3 Å/s | 3 Å/s (RF ion assisted 500 V) | RF 2.0 kW | 3 Å/s | RF 2.0 kW |
| Transfer rate | 58 mm/min | 58 mm/min | 2.9 m/min | 8 rpm (rotation) | 8 rpm (rotation) | 58 mm/min | 8 rpm (rotation) | 59 mm/min |
| Heater | None | None | None | None | None | None | None | None |
| Example | 1, 6-9 | 2 | — | 5 | — | 4 | 3 | — |
| Comparative example | — | — | 3 | — | 4 | — | — | 1 |

| | 2) Photocatalyst layer | | | | | 3) Hydrophilic thin film layer (overcoat) or peel preventing layer | |
|---|---|---|---|---|---|---|---|
| | TiO$_2$ | TiO$_2$ | TiO$_2$ (Zn, Mo, Fe doped) | | TiOxNy | SiO$_2$ | |
| | Sputtering | Deposition | Deposition | Sputtering | Sputtering | Sputtering | |
| Target | Ti | TiO | TiO | Ti (doped) | Ti | Si | |
| Gas | O$_2$: 100% | O$_2$: 100% | O$_2$: 60%, Ar: 40% | O$_2$: 100% | O$_2$: 97%, N$_2$: 3% | O$_2$: 50%, Ar: 50% | |
| Gas pressure | 0.93 Pa (7 m Torr) | 1.33 × 10$^{-2}$ Pa (1 × 10$^{-4}$ Torr) | 1.33 × 10$^{-2}$ Pa (1 × 10$^{-4}$ Torr) | 0.93 Pa (7 m Torr) | 0.93 Pa (7 m Torr) | 0.40 Pa (3 m Torr) | 0.93 Pa (7 m Torr) |
| Applied power, etc. | DC 2.88 kW | 3 Å/s | 3 Å/s | DC 2.88 kW | DC 2.88 kW | RF 2.0 kW | RF 2.0 kW |
| Transfer rate | 1 m/min | 8 rpm (rotation) | 8 rpm (rotation) | 1 m/min | 1 m/min | 1 m/min | 0.98 m/min |
| Heater | None | None | None | None | None | None | None |
| Example | 1, 2 | 5 | 3 | 6-9 | 4 | 1, 2 | 9 |
| Comparative example | 1-3, 11 | 4 | — | 5-10 | — | 1, 2 | 11 |

The number of the film formation pass was appropriately adjusted so as to achieve a predetermined thickness.

In the hydrophilicity evaluation, UV-θ1 method and UV-θ3 method were adopted in a case where a hydrophilic thin film was not coated, and while UV-θ2 method was adopted in a case where a hydrophilic thin film was coated. UV-θ1 method is a method in which irradiation with ultraviolet black light having an intensity of 1 mW/cm² is conducted for 15 minutes, and the contact angle with respect to pure water is measured immediately after completion of the irradiation. UV-θ3 method is a method in which the period of time for the ultraviolet light irradiation in UV-θ1 method is changed to 60 minutes. When the contact angle with respect to pure water is small, which means that the hydrophilicity is high, it can be said that the photocatalytic activity is high, and also the antifouling property is high. The overall evaluation was conducted based on the following reference.

| UV-θ1 method and UV-θ3 method Photocatalytic activity evaluation | Contact angle θ after ultraviolet light irradiation |
| --- | --- |
| Excellent (E) | $\theta \leq 5°$ |
| Good (G) | $5° < \theta < 10°$ |
| Mean (M) | $10° \leq \theta < 20°$ |
| Bad (B) | $20° \leq \theta$ |

UV-θ2 method was basically applied to a case where a hydrophilic thin film was coated onto the surface of a photocatalyst layer. In such a case where a hydrophilic thin film is coated, the initial contact angle is small, and thereby a comparison of the contact angles before ultraviolet light irradiation and after ultraviolet light irradiation is difficult. Therefore, liquid of 5 ml which constituted of hexane, 2-propanol and propionic acid at a ratio of 6:1:3 was applied onto the surface, and the contact angle change caused by ultraviolet light irradiation (1 mW/cm², 15 minutes) was measured. The contact angle immediately after completion of the ultraviolet light irradiation can be considered an index of the photocatalytic activity and the antifouling property. Also, the contact angle was measured after storage in the dark for 2 weeks subsequent to completion of the ultraviolet light irradiation, and the results ware used as an index of the maintenance performance of the hydrophilicity based on the following reference.

| UV-θ2 Performance evaluation | Contact angle θ' after storing in dark |
| --- | --- |
| Excellent (E) | $\theta' \leq 15°$ |
| Good (G) | $15° < \theta' \leq 25°$ |
| Mean (M) | $25° < \theta' < 30°$ |
| Bad (B) | $30° \leq \theta'$ |

Figure 4:
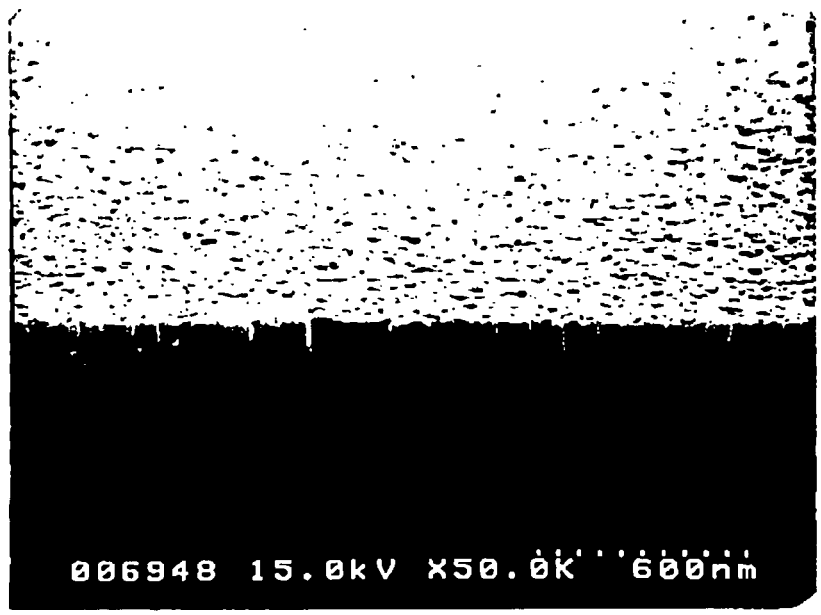
FIGS. 4(a) to (d) are scanning electron microscope (SEM) observation pictures for Examples 1 and 2 and Comparative Examples 1 and 2, respectively.
Figure 4:
Figure 4:
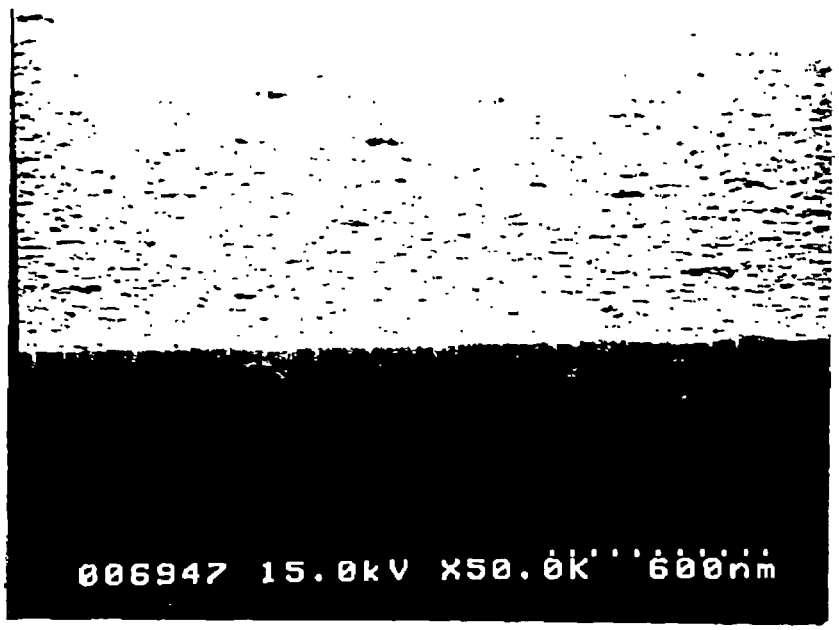
Figure 4:
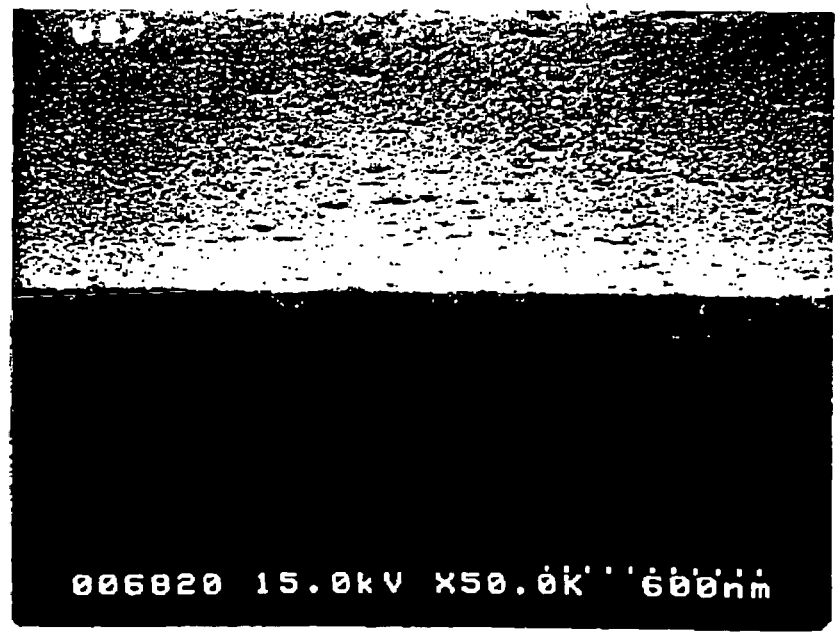

FIGS. 4(a) to (d) are scanning electron microscope (SEM) observation pictures for Examples 1 and 2 and Comparative Examples 1 and 2, respectively. As shown in FIGS. 4(a) and (b), a columnar particulate photocatalyst layer (TiO₂) is formed on the undercoat layer (crystalline ZrO₂) in Examples 1 and 2.

On the other hand, as shown in FIG. 4(c), in Comparative Example 1, although a columnar particulate photocatalyst layer (TiO₂) is formed, the thickness thereof is small, and a dead layer is formed around the interface between the amorphous undercoat layer (Si₃N₄) and the photocatalyst layer (TiO₂).

Also, as shown in FIG. 4(d), in Comparative Example 2 where no undercoat layer is provided, titanium oxide (TiO₂) in the photocatalyst layer does not grow into large particles, which suggests that the crystallinity is low.

Figure 5:
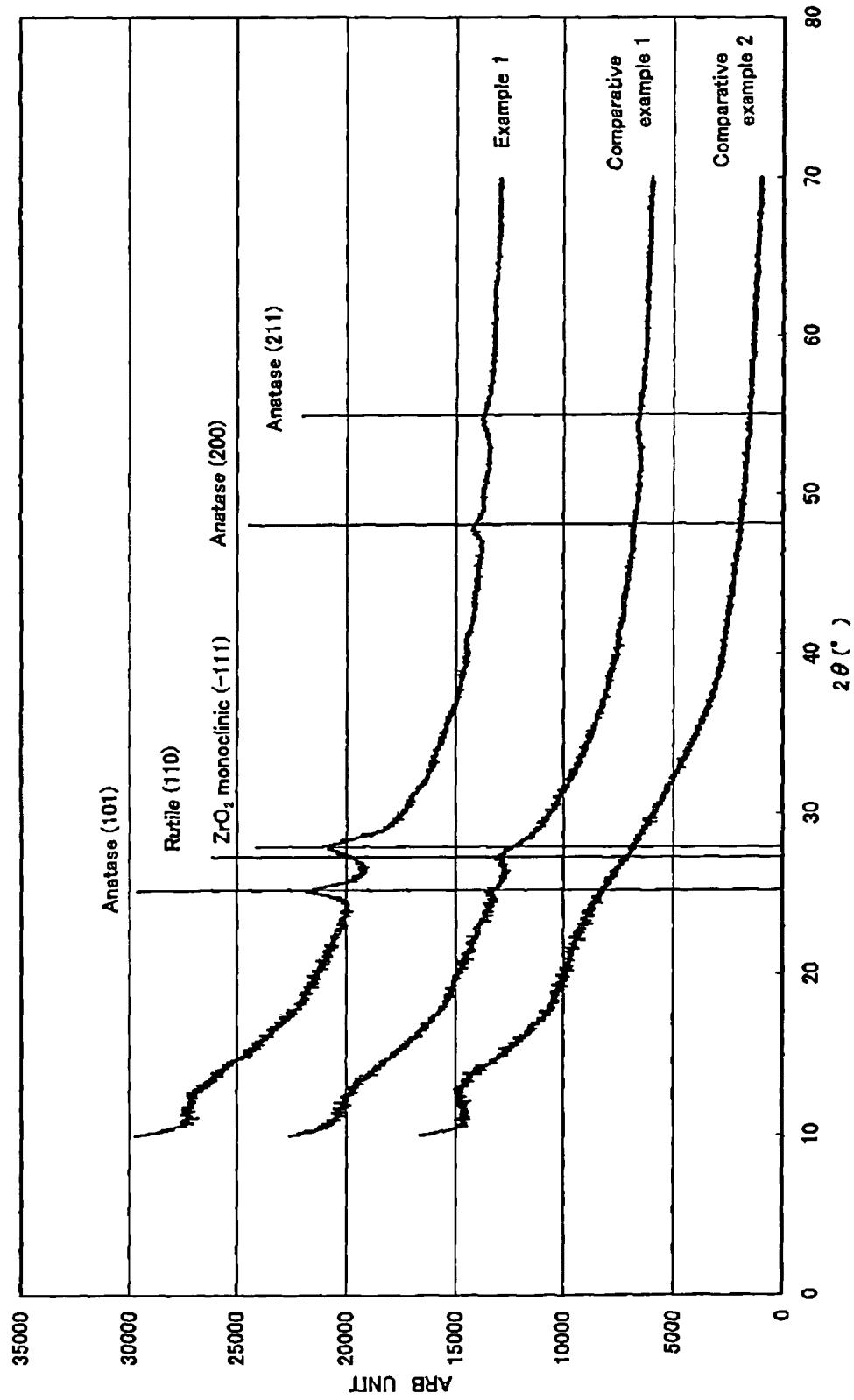
FIG. 5 is a graph showing the results of X-ray diffraction measurements in Example 1 and Comparative Examples 1 and 2 which shows the relationship between the undercoat layer and the crystallinity of $TiO_2$ in the photocatalyst layer.

FIG. 5 is a graph showing the results of thin film X-ray diffraction measurements for Example 1 and Comparative Examples 1 and 2. From the results, it was confirmed that TiO₂ of Example 1 where the undercoat layer was constituted of crystalline ZrO₂ showed a diffraction peak which was ascribable to anatase (101), and the crystallinity of the TiO₂ was high. On the other hand, TiO₂ of Comparative Example 1 where the undercoat layer was constituted of amorphous Si₃N₄ showed a crystal peak of rutile (110) to some extent, but did not show a crystal peak of anatase (101), and in Comparative Example 2 where no undercoat layer was provided, neither a crystal peak of anatase (101) nor a crystal peak of rutile (110) was observed. With this, it was confirmed that the crystallinity of the TiO₂ in Comparative Examples was low. The TiO₂ of Comparative Examples had low crystallinity or no crystallinity by the X-ray analysis, but it was confirmed that microcrystals of anatase or rutile were present on a dead layer which was observed as a halo pattern according to an electron diffraction. Such TiO₂ will be hereinafter referred to as low crystalline TiO₂.

As can be seen from the above-described experimental results, the presence of the dead layer prevents the particulate crystal structure of the photocatalyst layer from growing, which causes low photocatalytic activity. Specifically, it can be seen that the absence of the dead layer verifies the growth of the particulate crystal structure of the photocatalyst layer (TiO₂) which is necessary for exerting high photocatalytic activity. In order to prevent the dead layer from being generated, it is necessary that at least a crystalline undercoat layer is present under the photocatalyst layer, and it can be said that formation of an anatase type TiO₂ layer on a monoclinic ZrO₂ undercoat layer is most suitable for enhancing the crystallinity of TiO₂.

In Comparative Examples 3 and 4, a TiO₂ layer was formed on an amorphous ZrO₂ undercoat layer. In Comparative Example 3, the amorphous ZrO₂ layer was obtained by conducting film formation by transition mode sputtering. In Comparative Example 4, the amorphous ZrO₂ layer was obtained by employing an ion assisted deposition method so as to eject oxygen ions into a film and thereby disorder the structure of the film. The TiO₂ layer formed on such an amorphous ZrO₂ undercoat layer has low crystallinity, and a thick dead layer was formed in this instance, which is different from Examples where the TiO₂ layer was formed on the monoclinic ZrO₂ undercoat layer. Consequently, it is not the material of the undercoat layer but the crystallinity of the undercoat layer that affects the crystallinity of the TiO₂ layer.

Now, a brief description will be made below on the transition mode sputtering method which was employed for film formation of the zirconium oxide film in Comparative Example 3 and Comparative Example 13. In reactive sputtering from a metal target, when oxidation occurs on the surface of the metal target, the film formation rate comes to be lowered. Accordingly, by sensing the oxidation state of the target through monitoring the emission state of oxygen with a plasma emission monitor, and by performing feedback of the obtained information to the gas flow rate control system, it becomes possible to form an oxide film at a higher film formation rate. This method is referred to as a transition mode sputtering method.

Next, a description will be made below on the film formation examples with respect to the peel preventing layer formed between the substrate and the undercoat layer, and on the results of a salt spray test. Table 4 shows the film configuration, the methods of forming the peel preventing layer, the undercoat layer, the photocatalyst layer and the hydrophilic thin layer; the presence of a dead layer, the results of contact angle evaluation, and the results of a salt spray test in Examples 10 to 17 and Comparative Examples 12 and 13. Table 5 shows the film formation conditions for the peel preventing layer, and the film formation conditions for the other films (the undercoat layer and the photocatalyst layer).

TABLE 4

| | | Film configuration and film formation method | | | Electron diffraction & TEM measurement Presence/absence of dead layer | Contact angle evaluation results | |
|---|---|---|---|---|---|---|---|
| | Substrate | Peel preventing layer (thickness) Film formation method | Undercoat layer (thickness) Film formation method | Photo-catalyst layer (thickness) Film formation method | | UV-θ1 method Contact angle after UV irradiation Overall evaluation | Salt spray test Evaluation results |
| Ex. 10 | Glass (bottom face) | $SiO_2$ (20 nm) Sputtering | Monoclinic $ZrO_2$ (56 nm) Sputtering | Anatase $TiO_2$ (140 nm) Sputtering | Absent | 5° E | G |
| Ex. 11 | Glass (bottom face) | $SiO_2$ (20 nm) Sputtering | Monoclinic $ZrO_2$ (56 nm) Sputtering (15 m torr) | Anatase $TiO_2$ (140 nm) Sputtering | Absent | 4° E | G |
| Ex. 12 | Glass (bottom face) | $SiO_2$ (20 nm) Sputtering | Monoclinic $ZrO_2$ (56 nm) Sputtering | Anatase $TiO_2$ (50 nm) Sputtering | Absent | 9° G | G |
| Ex. 13 | Glass (bottom face) | $SiOxNy$ (20 nm) Sputtering | Monoclinic $ZrO_2$ (56 nm) Sputtering | Anatase $TiO_2$ (50 nm) Sputtering | Absent | 9° G | G |
| Ex. 14 | Glass (top face) | $SixNy$ (20 nm) Sputtering | Monoclinic $ZrO_2$ (56 nm) Sputtering | Anatase $TiO_2$ (50 nm) Sputtering | Absent | 9° G | G |
| Ex. 15 | Glass (top face) | $SnO_2$ (20 nm) Sputtering | Monoclinic $ZrO_2$ (56 nm) Sputtering | Anatase $TiO_2$ (50 nm) Sputtering | Absent | 9° G | G |
| Ex. 16 | Glass (bottom face) | ←Tin modification layer | Monoclinic $ZrO_2$ (56 nm) Sputtering | Anatase $TiO_2$ (50 nm) Sputtering | Absent | 9° G | M |
| Ex. 17 | Glass (top face) | $SiO_2$ (20 nm) Sputtering | Monoclinic $ZrO_2$ (56 nm) Sputtering | Anatase $TiO_2$ (150 nm) Sputtering | Absent | 5° E | G |
| Com. ex. 12 | Glass (top face) | | | Low crystallinity $TiO_2$ (50 nm) Baking, 250° C., 1 hr after sputtering | Present (ca. 50 nm thick) | 30° B | B |
| Com. ex. 13 | Glass (top face) | | Amorphous $ZrO_2$ (56 nm) Transition mode sputtering | Low crystallinity $TiO_2$ (50 nm) Baking, 250° C., 1 hr after sputtering | Present (ca. 50 nm thick) | 31° B | B |

TABLE 5

Film formation conditions
(Film formation conditions for the films in Table 4)

1) Peel preventing layer

| | $SiO_2$ Sputtering | $SiOxNy$ Sputtering | $SixNy$ Sputtering | $SnO_2$ Sputtering |
|---|---|---|---|---|
| Target | Si | Si | Si | Sn |
| Gas | $O_2$: 50%, Ar: 50% | $N_2$: 50%, $O_2$: 50% | $N_2$: 100% | $O_2$: 100% |
| Gas pressure | 0.93 Pa (7 m Torr) | 0.93 Pa (7 m Torr) | 0.93 Pa (7 m Torr) | 0.93 Pa (7 m Torr) |
| Applied power, etc. | RF 2.0 kW | RF 2.0 kW | RF 2.0 kW | DC 2.4 kW |
| Transfer rate | 1 m/min | 500 mm/min | 177 mm/min | 665 mm/min |
| Heater | None | None | None | None |
| Example | 10-12, 17 | 13 | 14 | 15 |
| Comparative example | — | — | — | — |

TABLE 5-continued

Film formation conditions
(Film formation conditions for the films in Table 4)

|  | 2) Undercoat layer | | | 3) Photocatalyst layer |
| --- | --- | --- | --- | --- |
|  | $ZrO_2$ Sputtering | $ZrO_2$ Sputtering | $ZrO_2$ Transition mode sputtering | $TiO_2$ Sputtering |
| Target | Zr | Zr | Zr | Ti |
| Gas | $O_2$: 100% | $O_2$: 100% | $O_2$: 30%, Ar: 70% | $O_2$: 100% |
| Gas pressure | 0.93 Pa (7 m Torr) | 2.0 Pa (15 m Torr) | 0.93 Pa (7 m Torr) | 0.93 Pa (7 m Torr) |
| Applied power, etc. | DC pulse 100 khz 5.5 kW | DC pulse 100 khz 5.5 kW | DC pulse 100 khz 2.0 kW | DC: 2.88 kW |
| Transfer rate | 1 m/min | 1 m/min | 2.9 m/min | 1 m/min |
| Heater | None | None | None | None |
| Example | 10, 12-17 | 11 | — | 10-17 |
| Comparative example | — | — | 13 | 12, 13 |

The number of the film formation pass was appropriately adjusted so as to achieve a predetermined thickness.

The salt spray test was conducted as follows:
Sodium chloride (extra pure reagent) was dissolved into ion-exchange water to prepare about 5% saline water. A test sample of 100×100 mm was fixed in an apparatus (CASSER-ISO-3, manufactured by Suga Test Instruments Co., Ltd.) so as to incline by 20±5 degrees from the vertical line, and the saline water was sprayed onto the test sample at a rate of 1 to 2 ml/hr. After the continuous spraying for 120 hours, the test sample was taken out and film peeling was observed.

The durability with respect to saline water was evaluated according to the following classification:

G (Good) . . . No film peeling and defect can be observed by a visual inspection and with an optical microscope.

M (Mean) . . . Defects can be partly observed with an optical microscope.

B (Bad) . . . Film peeling can be observed by a visual inspection or with an optical microscope.

According to the test results shown in Table 4, a peel preventing layer ($SiO_2$, SixNy, $SnO_2$, and SiOxNy) was formed on the glass substrate, and no film peeling and no defect was observed by a visual inspection and with an optical microscope in Examples 10 to 15 and 17. In Example 16 where the undercoat layer and the photocatalyst layer were formed directly on the bottom face of a glass substrate manufactured by a float process, since the tin modification layer present on the bottom face blocks various kinds of ions and molecules to some extent, no film peeling was observed by a visual inspection and with an optical microscope, and defects were only partly observed with an optical microscope. In Comparative Examples 12 and 13 where no peel preventing layer was provided, film peeling was observed.

Figure 6:
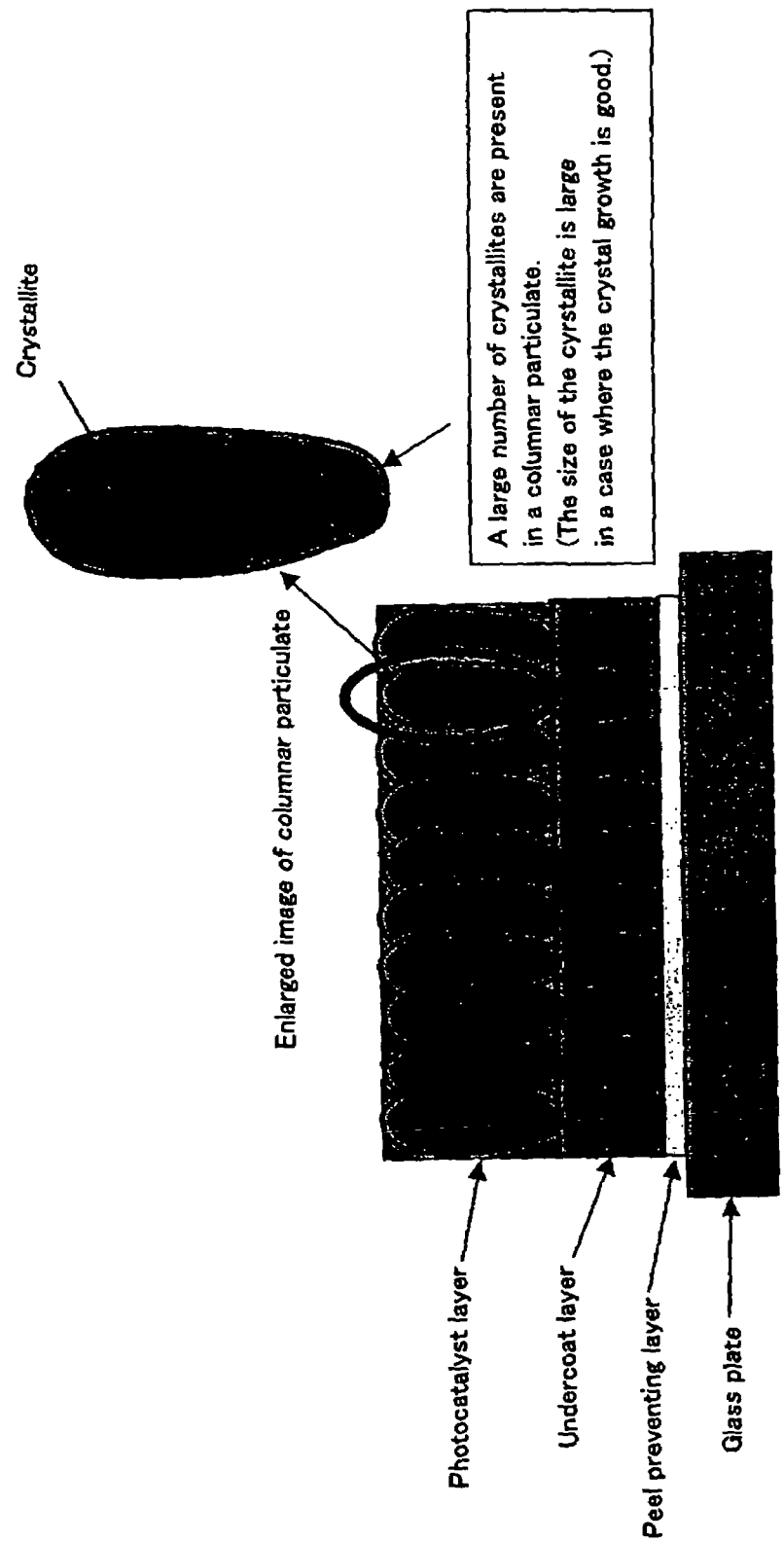
FIG. 6 is a schematic cross-sectional view illustrating another embodiment of a member having a photocatalytic function according to the present invention.

Next, a description will be made below on another embodiment of the present invention with reference to FIG. 6. A description will be omitted on the same matters as the above-described Examples. FIG. 6 is another cross-sectional view of a member having a photocatalytic function according to present invention, which shows a schematic diagram illustrating the relationship between the columnar particulate structure of the film and the crystallites. In this embodiment, a peel preventing layer is formed on the surface of a glass plate as a substrate, a monoclinic $ZrO_2$ layer is formed as an undercoat layer, and a crystalline $TiO_2$ layer is formed as a photocatalyst layer on the monoclinic $ZrO_2$ layer.

Table 6 shows Examples 18 to 26 and Comparative Examples 14 to 16 with respect to the relatively thin peel preventing layer, the monoclinic $ZrO_2$ undercoat layer and the photocatalyst layer.

TABLE 6

Examples and comparative examples with respect to the peel preventing layer thin film
and the monoclinic undercoat layer thin film

|  | Substrate | Peel preventing layer (thickness) | Undercoat layer (thickness) | Photocatalyst layer (thickness) | UV-θ3 | Salt spray test | Mechanical durability |
| --- | --- | --- | --- | --- | --- | --- | --- |
| Ex. 18 | Glass (top face) | $SiO_2$ (10 nm) | (10 nm) | $TiO_2$ (10 nm) | 6° | G | G |
| Ex. 19 | Glass (top face) | $SiO_2$ (5 nm) | (10 nm) | $TiO_2$ (10 nm) | 6° | G | G |
| Ex. 20 | Glass (top face) | $SiO_2$ (2 nm) | (10 nm) | $TiO_2$ (10 nm) | 8° | M | G |
| Ex. 21 | Glass (top face) | $SiO_2$ (10 nm) | Monoclinic $ZrO_2$ (5 nm) | $TiO_2$ (5 nm) | 7° | G | G |
| Ex. 22 | Glass (top face) | $SiO_2$ (5 nm) | Monoclinic $ZrO_2$ (5 nm) | $TiO_2$ (5 nm) | 7° | G | G |
| Ex. 23 | Glass (top face) | $SiO_2$ (10 nm) | Monoclinic $ZrO_2$ (3 nm) | $TiO_2$ (3 nm) | 10° | G | M |
| Ex. 24 | Glass (top face) | $SiO_2$ (10 nm) | Monoclinic $ZrO_2$ (5 nm) | $TiO_2$ (10 nm) | 7° | G | G |
| Ex. 25 | Glass (top face) | $SiO_2$ (10 nm) | Monoclinic $ZrO_2$ (2 nm) | $TiO_2$ (10 nm) | 9° | G | G |
| Ex. 26 | Glass (top face) | $SiO_2$ (10 nm) | (10 nm) | $TiO_2$ (600 nm) | 2° | G | M |

TABLE 6-continued

Examples and comparative examples with respect to the peel preventing layer thin film and the monoclinic undercoat layer thin film

|  | Substrate | Peel preventing layer (thickness) | Undercoat layer (thickness) | Photocatalyst layer (thickness) | UV-θ3 | Salt spray test | Mechanical durability |
|---|---|---|---|---|---|---|---|
| Com. ex. 14 | Glass (top face) | SiO$_2$ (0.5 nm) | Monoclinic ZrO$_2$ (5 nm) | TiO$_2$ (10 nm) | 6° | B | M |
| Com. ex. 15 | Glass (top face) | SiO$_2$ (10 nm) | — | TiO$_2$ (10 nm) | 52° (No catalytic activity) | G | G |
| Com. ex. 16 | Glass (top face) | — | (10 nm) | TiO$_2$ (10 nm) | 7° | B | G |

(Note)
The average temperature of the substrate at the time of each film formation was about 60° C. (based on thermolabel).
Only in Example 26, the average temperature of the substrate at the time of each film formation was about 120° C. (based on thermolabel).

The mechanical durability test shown in Table 6 was conducted by the following procedure, conditions, evaluation reference:

1) The abrasion resistance test was conducted by using a Taber testing machine under the conditions that the load was 500 g, the number of rotation was 10, and the speed of rotation was 60 rpm.

2) Ultrasonic cleaning was conducted for 5 minutes in acetone, and thereafter UV ozone cleaning was conducted for 3 minutes.

3) Observation and evaluation of the sample were made by a visual inspection.

Evaluation Reference
G (Good): No problem.
M (Mean): Abrasive scratches were partly observed.
B (Bad): Film peeling partly occurred.

Figure 7:
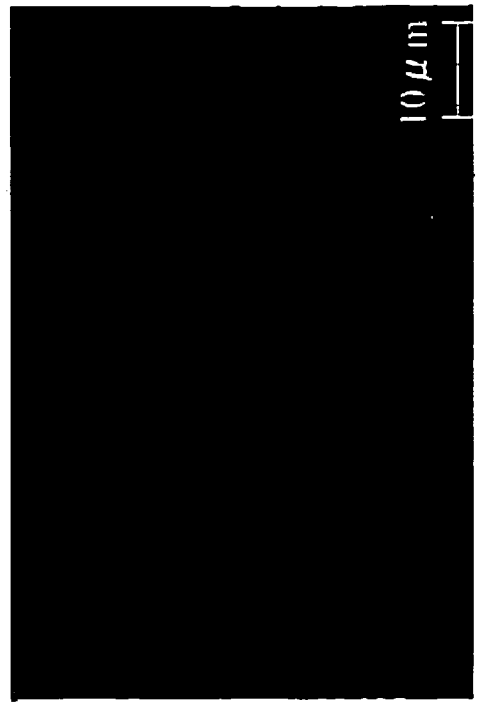
FIG. 7 shows optical microscope pictures of the surfaces of Example 18 and Comparative Example 16 after a salt spray test which show the effect of the peel preventing layer.
Figure 7:
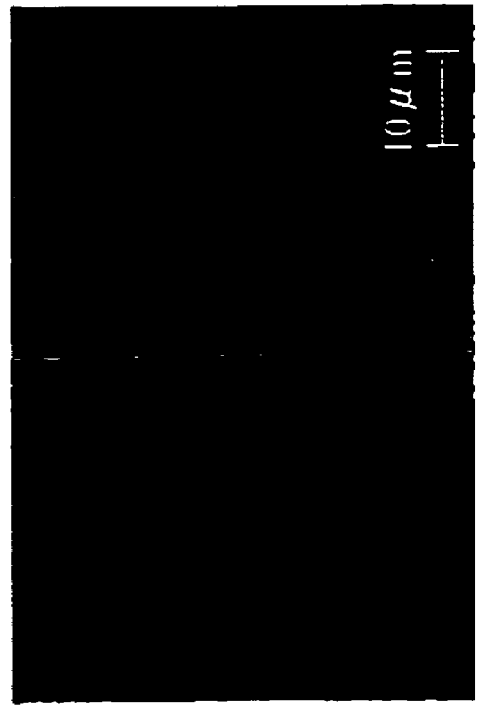

Table 7 shows the film formation conditions for each film (the peel preventing layer, the undercoat layer, and the photocatalyst layer) of Examples 18 to 26 shown in Table 6. FIG. 7 also shows the optical microscope pictures of Example 18 (having a peel preventing layer) and Comparative Example 16 (having no peel preventing layer) after a salt spray test. No film peeling was observed in Example 18 having a peel preventing layer, while spot-like film peeling was observed in Comparative Example 16 having no peel preventing layer, which verifies the effect of the peel preventing layer.

From the above-described results, it was confirmed that the peel preventing layer, the undercoat layer and the photocatalyst layer are excellent in the contact angle evaluation results, the salt spray test results and the mechanical durability even if the peel preventing layer, the undercoat layer and the photocatalyst layer has a small thickness of around 5 to 10 nm. When each layer has a small thickness as described above, a photocatalytic member in which the reflectance is low, the reflection color tone is neutral and the color tone unevenness is absent can be obtained, and such a member can be suitably applied particularly to glass for use in construction.

TABLE 7

Experimental conditions for the examples in Table 6

1) Peel preventing layer

|  | SiO$_2$ Sputtering |
|---|---|
| Target | Si |
| Gas | O$_2$: 50%, Ar: 50% |
| Gas pressure | 0.93 Pa (7 m Torr) |

TABLE 7-continued

Experimental conditions for the examples in Table 6

| Electric power supply, etc. | DC |
|---|---|
| Transfer rate | 1 m/min |
| Heater | None |
| Example | 18-26 |
| Comparative example | 14, 15 |

2) Undercoat layer

|  | ZrO$_2$ Sputtering |
|---|---|
| Target | Zr |
| Gas | O$_2$: 100% |
| Gas pressure | 0.93 Pa (7 m Torr) |
| Electric power supply, etc. | DC pulse |
| Transfer rate | 1 m/min |
| Heater | None |
| Example | 18-26 |
| Comparative example | 14, 16 |

3) Photocatalyst layer

|  | TiO$_2$ Sputtering |
|---|---|
| Target | Ti |
| Gas | O$_2$: 100% |
| Gas pressure | 0.93 Pa (7 m Torr) |
| Electric power supply, etc. | DC |
| Transfer rate | 1 m/min |
| Heater | None |
| Example | 18-26 |
| Comparative example | 14, 16 |

The applied power and the number of the film formation pass were appropriately adjusted so as to achieve a predetermined thickness.

Table 8 shows a comparison of the hydrophilization properties and the film formation rate of the titanium tin oxide layer on the monoclinic ZrO$_2$ undercoat layer in Examples 18 and 27 to 29. Table 9 shows the film formation conditions for the photocatalyst layer of Examples in Table 8, wherein the film formation conditions for the other layers, i.e., the peel preventing layer and the undercoat layer are the same as those shown in Table 7. It can be seen that the use of titanium oxide to which tin is added improves the hydrophilicity maintenance property in the dark. Also, it can be confirmed that the addition of tin improves the film formation rate in a sputtering method.

Table 10 shows the X-ray diffraction results and the TEM observation results with respect to the sample of Examples 18 and 17. It is apparent from Table 10 that the ZrO$_2$ undercoat layer is monoclinic, and the crystal structure of the photocatalyst layer TiO$_2$ is an anatase structure.

TABLE 8

Comparison of the hydrophilization properties and the film formation rate of the titanium tin oxide formed on the monoclinic undercoat layer film

| | Substrate | Peel preventing layer (thickness) | Undercoat layer (thickness) | Photocatalyst layer (thickness) | UV-θ3 | Hydrophilicity maintenance property in dark (Note 1) | (Ti—Sn film formation rate)/ (Ti film formation rate) |
|---|---|---|---|---|---|---|---|
| Ex. 18 | Glass | SiO$_2$ (10 nm) | Monoclinic ZrO$_2$ (10 nm) | TiO$_2$ (10 nm) | 6° | 25° | 1.0 |
| Ex. 27 | Glass | SiO$_2$ (10 nm) | Monoclinic ZrO$_2$ (10 nm) | Sn (5 at %) doped TiO$_2$ (10 nm) | 6° | 18° | 1.2 |
| Ex. 28 | Glass | SiO$_2$ (10 nm) | Monoclinic ZrO$_2$ (10 nm) | Sn (30 at %) doped TiO$_2$ (10 nm) | 8° | 16° | 1.9 |
| Ex. 29 | Glass | SiO$_2$ (10 nm) | Monoclinic ZrO$_2$ (10 nm) | Sn (45 at %) doped TiO$_2$ (10 nm) | 10° | 15° | 3.0 |

X-ray diffraction profile measurement shows that these tin doped photocatalyst films are excellent in crystallinity and tend to have rutile crystallinity.
Note 1)
After measurement was made by UV-θ3 procedure, the sample was stored in the dark for 1 week, and thereafter the contact angle with respect to pure water (while being increased) was measured.

TABLE 9

(Experimental conditions for Examples in Table 8) Photocatalyst layer

| | TiO$_2$ | | | |
|---|---|---|---|---|
| | Sputtering | Sputtering | Sputtering | Sputtering |
| Target | Ti | Ti—Sn (Sn: 5 at %) | Ti—Sn (Sn: 30 at %) | Ti—Sn (Sn: 45 at %) |
| Gas | O$_2$: 100% | O$_2$: 100% | O$_2$: 100% | O$_2$: 100% |
| Gas pressure | 0.93 Pa (7 m Torr) | 0.93 Pa (7 m Torr) | 0.93 Pa (7 m Torr) | 0.93 Pa (7 m Torr) |
| Electric power supply, etc. | DC | DC | DC | DC |
| Transfer rate | 1 m/min | 1 m/min | 1 m/min | 1 m/min |
| Heater | None | None | None | None |
| Example | 18 | 27 | 28 | 29 |

The peel layers and undercoat layers were embodied under the same conditions as those shown in Table 7.
The applied power and the number of the film formation passes were appropriately adjusted for the purpose of achieving the respective predetermined thicknesses.

TABLE 10

Interplanar spacing and Miller indices measured from the TEM bright-field image

| | | Interplanar spacing and crystal system of ZrO$_2$ in JCPDS | | Interplanar spacing and crystal system of TiO$_2$ in JCPDS | |
|---|---|---|---|---|---|
| | Observed Observed with a loupe | ZrO$_2$ Monoclinic | Other crystal systems were denied from an XD peak. | Anatase | Other crystal systems were denied from an XD peak. |
| (a) Glass/SiO$_2$ (10 nm)/ZrO$_2$ (10 nm)/TiO$_2$ (10 nm) (Sample of Example 18 and FIG. 8) | | | | | |
| ZrO$_2$ | 2.867 | (111) 2.841 | | | |
| | 3.185 | (−111) 3.165 | | | |
| | 3.358 | (−111) 3.165 | | | |
| TiO$_2$ | 3.544 | | | (101) 3.520 | |
| | 3.503 | | | (101) 3.520 | |
| (b) Glass/SiO$_2$ (20 nm)/ZrO$_2$ (100 nm)/TiO$_2$ (150 nm) (Sample of Example 17 and FIG. 9) | | | | | |
| ZrO$_2$ | 2.831 | (111) 2.841 | | | |
| | 3.109 | (−111) 3.165 | | | |
| | 3.731 | (−111) 3.698 | | | |
| TiO$_2$ | 3.449 | | | (101) 3.520 | |

The film formation conditions follow Table 7.

Figure 8:
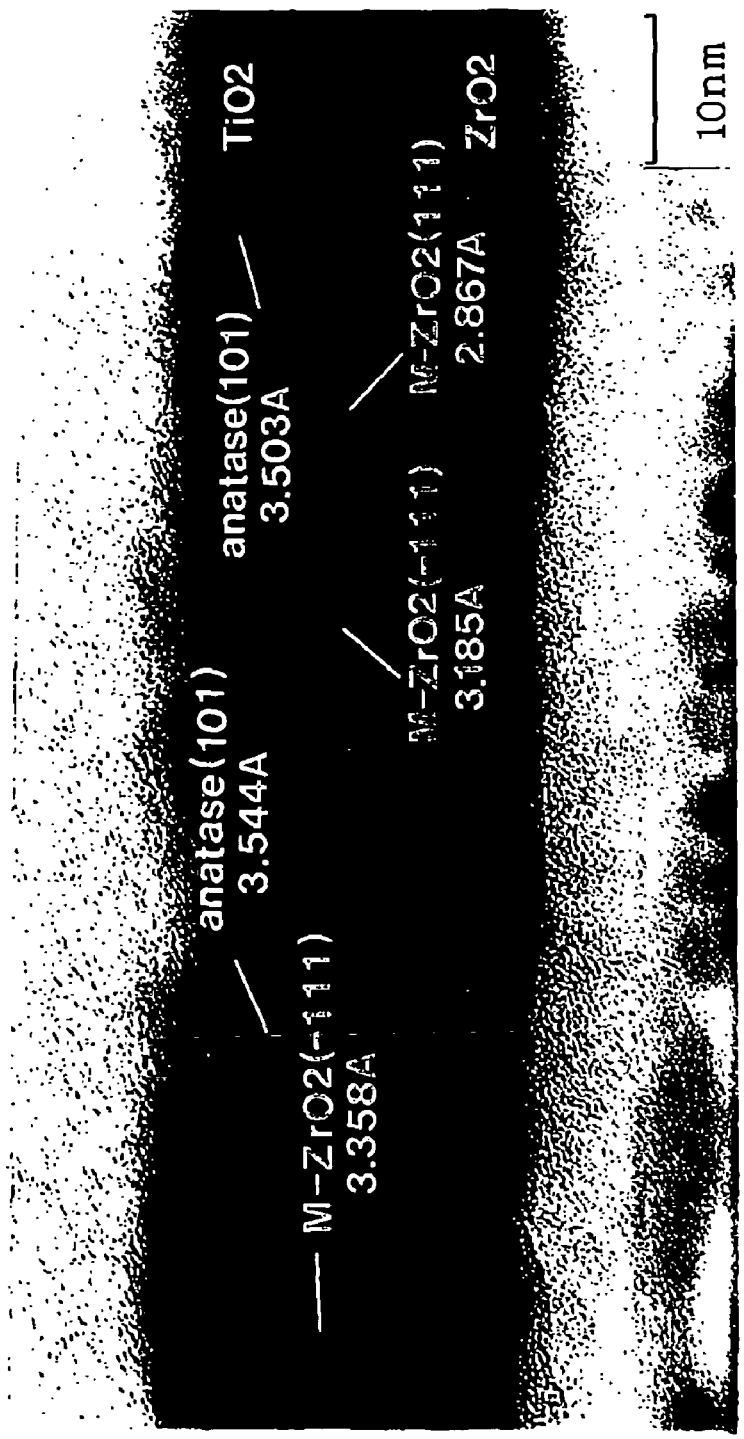
FIG. 8 is a high resolution TEM picture which shows the cross section of the $ZrO_2$ layer and the $TiO_2$ layer in Example 18.

In order to verify the above-described results, a high resolution TEM picture of Example 18 is shown in FIG. 8. FIG. 8 shows a structure in which the (−111) plane of $ZrO_2$ (monoclinic) is continuous with the (101) plane of $TiO_2$ (anatase) with an inclination is observed in the $TiO_2$ film which is grown on the $ZrO_2$ film.

Figure 9:
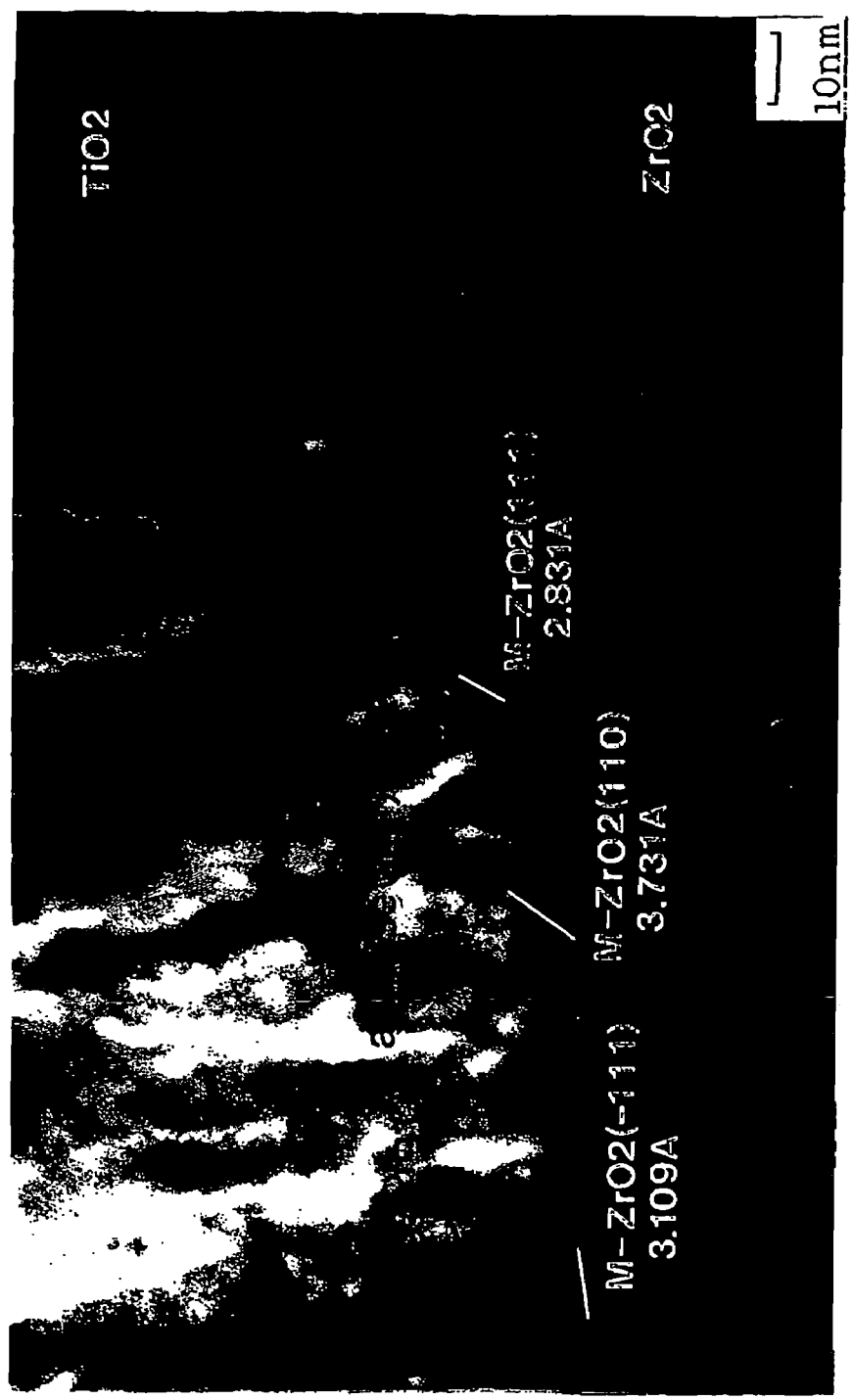
FIG. 9 is a high resolution TEM picture which shows the cross section of the $ZrO_2$ layer and the $TiO_2$ layer in Example 17.
Figure 10:
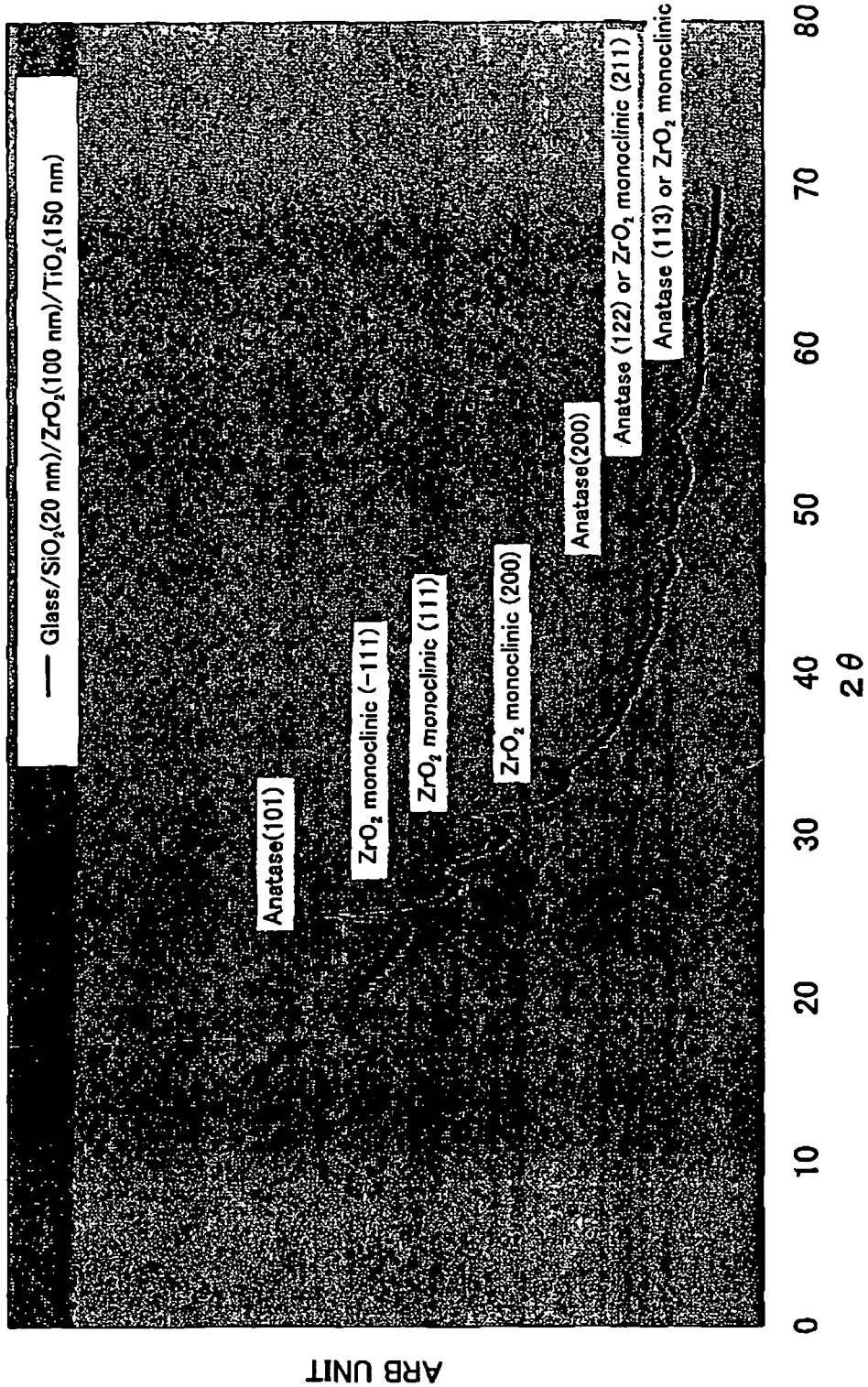
FIG. 10 is an X-ray diffraction profile of the sample in Example 17.

A high resolution TEM picture of the cross section of the $ZrO_2$ film and the $TiO_2$ film in Example 17 is shown in FIG. 9. The $ZrO_2$ film and the $TiO_2$ film in Example 17 has a thickness of 10 times or more compared to each film in Example 18. A lattice pattern is found on the interface with respect to each thin film, and this figure shows that a structure in which the monoclinic $ZrO_2$ (−111) plane is continuous with the anatase type $TiO_2$ (101) plane is observed. This figure also shows that the monoclinic $ZrO_2$ (110) plane is continuous with the anatase type $TiO_2$ (101) plane in some portions. FIG. 10 shows an X-ray diffraction profile of Example 17, in which peaks of the anatase type $TiO_2$ and the monoclinic $ZrO_2$ were observed.

INDUSTRIAL APPLICABILITY

As described above, when a photocatalyst layer is formed on the surface of a substrate, by providing a crystalline (monoclinic) undercoat layer and forming the photocatalyst layer on the undercoat layer, the photocatalyst crystals are allowed to grow continuously up to the surface of the photocatalyst layer. Also, by providing a peel preventing layer between the substrate and the undercoat layer, peeling and defects can be controlled. As a result, it is possible to obtain a member having high photocatalytic activity and a high antifouling property which can be applied to all the members for use in glass panes for construction, glass plates for displays, glass substrates for DNA analysis, portable information devices, sanitary equipments, medical care equipments, biomedical test chips, materials for hydrogen/oxygen generation devices, and the like.

Also, by forming the peel preventing layer whose main component is an oxide, an oxynitride and a nitride containing at least one of silicon and tin on the surface of the substrate, forming the monoclinic zirconium oxide layer, for example, at low temperature of 150° C. or below, and thereafter forming the photocatalyst layer comprising a crystalline phase, it becomes possible to combine with a material having low heat resistance. In addition, since precise control of the temperature distribution in heating is not required, the present invention can be applied to film formation on a large size plate glass easily.

The invention claimed is:

1. A member having a photocatalytic function comprising:
a substrate;
an undercoat layer provided on said substrate, the undercoat layer including monoclinic zirconium oxide; and
a photocatalyst layer formed on said undercoat layer, the photocatalyst layer including anatase type titanium dioxide,
wherein said undercoat layer is crystalline, said photocatalyst layer is constituted of a crystalline phase, and no dead layer which is observed as a halo pattern in an electron diffraction image is substantially present between said undercoat layer and said photocatalyst layer,
wherein an electron diffraction image obtained by perpendicularly irradiating a cross section of the undercoat layer includes an electron diffraction image from a (111) orientation plane or a (−111) plane of the monoclinic zirconium oxide, an interplanar spacing with respect to the (111) orientation plane measured by an electron diffraction image or by a bright-field image of a transmission electron microscope (TEM) is 2.6 to 3.0 Å, and an interplanar spacing with respect to the (−111) orientation plane measured by the an electron diffraction image or by a bright field image of a transmission electron microscope (TEM) is 3.0 to 3.5 Å, and wherein at least one of the distances between oxygen atoms in crystals which constitute the undercoat layer is in the range from 90 to 110%with respect to at least one of the distances between oxygen atoms in crystals which constitute the photocatalyst layer.

2. A member having a photocatalytic function comprising:
a substrate;
a peel preventing layer, whose main component is an oxide, an oxynitride or a nitride of at least one of silicon and tin, provided on a surface of said substrate;
an undercoat layer provided on said peel preventing layer, the undercoat layer including monoclinic zirconium oxide; and
a photocatalyst layer formed on a surface of said undercoat layer, the photocatalyst layer including anatase type titanium dioxide,
wherein said undercoat layer is crystalline, said photocatalyst layer is constituted of a crystalline phase, and no dead layer which is observed as a halo pattern in an electron diffraction image is substantially present between said undercoat layer and said photocatalyst layer,
wherein an electron diffraction image obtained by perpendicularly irradiating a cross section of the undercoat layer includes an electron diffraction image from a (111) orientation plane or a (−111) plane of the monoclinic zirconium oxide, an interplanar spacing with respect to the (111) orientation plane measured by an electron diffraction image or by a bright-field image of a transmission electron microscope (TEM) is 2.6 to 3.0 Å, and an interplanar spacing with respect to the (−111) orientation plane measured by the an electron diffraction image or by a bright field image of a transmission electron microscope (TEM) is 3.0 to 3.5 Å, and wherein at least one of the distances between oxygen atoms in crystals which constitute the undercoat layer is in the range from 90 to 110%with respect to at least one of the distances between oxygen atoms in crystals which constitute the photocatalyst layer.

3. The member having a photocatalytic function according to claim 2, wherein said peel preventing layer has a thickness of from 2 nm to 200 nm.

4. The member having a photocatalytic function according to claim 2, wherein said substrate is a glass plate manufactured by a float process, and said peel preventing layer is a tin modification layer formed on a bottom face of said glass plate at a time of manufacturing said glass plate.

5. The member having a photocatalytic function according to claim 2, wherein said dead layer has a thickness of 0 nm or more and 20 nm or less.

6. The member having a photocatalytic function according to claim 2, wherein said photocatalyst layer has a thickness of from 1 nm to 1,000 nm.

7. The member having a photocatalytic function according to claim 2, wherein said undercoat layer has a thickness of from 1 nm to 500 nm.

8. The member having a photocatalytic function according to claim 2, wherein particulates which constitute said photocatalyst layer are formed continuously from an interface with the undercoat layer to a surface of the photocatalyst layer.

9. The member having a photocatalytic function according to claim 8, wherein a width of the particulates which constitute said photocatalyst layer along a direction parallel to the substrate is 5 nm or more.

10. The member having a photocatalytic function according to claim 2, wherein an electron diffraction image obtained by perpendicularly irradiating a cross section of the photocatalyst layer includes an electron diffraction pattern from the (101) plane of the anatase type titanium oxide, and an interplanar spacing with respect to the (101) orientation plane measured by an electron diffraction image or by a bright-field image of a transmission electron microscope (TEM) is 3.3 to 3.7 Å.

11. The member having a photocatalytic function according to claim 2, wherein a metal element is doped in said photocatalyst layer.

12. The member having a photocatalytic function according to claim 11, wherein said metal element is at least one of Sn, Zn and Mo.

13. The member having a photocatalytic function according to claim 11, wherein an addition amount of said metal element is 0.1 mass % or more and 1.0 mass % or less.

14. The member having a photocatalytic function according to claim 11, wherein an addition amount of said metal element is 0.2 mass % or more and 0.5 mass % or less.

15. The member having a photocatalytic function according to claim 11, wherein said metal element is Fe and an addition amount thereof is 0.001 mass % or more and 1.0 mass % or less.

16. The member having a photocatalytic function according to claim 2, wherein a hydrophilic thin film is formed on the surface of said photocatalyst layer.

17. The member having a photocatalytic function according to claim 16, wherein said hydrophilic thin film is made of at least one oxide selected from the group consisting of silicon oxide, zirconium oxide, germanium oxide and aluminum oxide.

18. The member having a photocatalytic function according to claim 17, wherein said hydrophilic thin film is made of silicon oxide.

19. The member having a photocatalytic function according to claim 16, wherein said hydrophilic thin film is porous.

20. The member having a photocatalytic function according to claim 16, wherein said hydrophilic thin film has a thickness of 1 nm or more and 30 nm or less.

21. The member having a photocatalytic function according to claim 16, wherein said hydrophilic thin film has a thickness of 1 nm or more and 20 nm or less.

22. The member having a photocatalytic function according to claim 2, wherein at least said undercoat layer and said photocatalyst layer are formed by a vapor phase method.

23. The member having a photocatalytic function according to claim 22, wherein said vapor phase method is a sputtering method.

24. A method for manufacturing a photocatalytic member comprising the steps of:
    forming a peel preventing layer whose main component is an oxide, an oxynitride or a nitride containing at least one of silicon and tin on the surface of a substrate;
    forming an undercoat layer including monoclinic zirconium oxide at low temperature on said peel preventing layer; and
    forming a photocatalyst layer including anatase type titanium dioxide on said undercoat layer, wherein said undercoat layer is crystalline, said photocatalyst layer is constituted of a crystalline phase, and no dead layer which is observed as a halo pattern in an electron diffraction image is substantially present between said undercoat layer and said photocatalyst layer,
    wherein an electron diffraction image obtained by perpendicularly irradiating a cross section of the undercoat layer includes an electron diffraction image from a (111) orientation plane or a (-111) plane of the monoclinic zirconium oxide, an interplanar spacing with respect to the (111) orientation plane measured by an electron diffraction image or by a bright-field image of a transmission electron microscope (TEM) is 2.6 to 3.0 Å, and an interplanar spacing with respect to the (-111) orientation plane measured by the an electron diffraction image or by a bright field image of a transmission electron microscope (TEM) is 3.0 to 3.5 Å.

25. The method for manufacturing a photocatalytic member according to claim 24, wherein said undercoat layer is formed at temperature of 150C. or below.

26. The method for manufacturing a photocatalytic member according to claim 24, wherein said undercoat layer is formed by a sputtering method.

* * * * *

UNITED STATES PATENT AND TRADEMARK OFFICE
CERTIFICATE OF CORRECTION

| | | |
|---|---|---|
| PATENT NO. | : 7,612,015 B2 | Page 1 of 1 |
| APPLICATION NO. | : 10/499462 | |
| DATED | : November 3, 2009 | |
| INVENTOR(S) | : Anzaki et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1069 days.

Signed and Sealed this

Nineteenth Day of October, 2010

David J. Kappos
*Director of the United States Patent and Trademark Office*